(12) United States Patent
Maurer

(10) Patent No.: US 11,504,492 B2
(45) Date of Patent: Nov. 22, 2022

(54) AIR CONDUIT FOR A RESPIRATORY DEVICE

(71) Applicant: ResMed Pty Ltd, Bella Vista (AU)

(72) Inventor: Dimitri Marco Maurer, Gosford (AU)

(73) Assignee: ResMed Pty Ltd, Bella Vista (AU)

( * ) Notice: Subject to any disclaimer, the term of this patent is extended or adjusted under 35 U.S.C. 154(b) by 581 days.

(21) Appl. No.: 15/765,733

(22) PCT Filed: Oct. 7, 2016

(86) PCT No.: PCT/AU2016/050942
§ 371 (c)(1),
(2) Date: Apr. 4, 2018

(87) PCT Pub. No.: WO2017/059494
PCT Pub. Date: Apr. 13, 2017

(65) Prior Publication Data
US 2018/0296787 A1    Oct. 18, 2018

(30) Foreign Application Priority Data
Oct. 8, 2015  (AU) .................. 2015904092

(51) Int. Cl.
*A61M 16/08*    (2006.01)
*A61M 16/10*    (2006.01)
(Continued)

(52) U.S. Cl.
CPC .... *A61M 16/0816* (2013.01); *A61M 16/0611* (2014.02); *A61M 16/0666* (2013.01);
(Continued)

(58) Field of Classification Search
CPC . F16L 53/00; F16L 53/30; F16L 53/34; F16L 11/16; F16L 11/18
See application file for complete search history.

(56) References Cited

U.S. PATENT DOCUMENTS 3,122,171 A * 2/1964 Philips .............. F16L 11/16
138/129
4,203,476 A * 5/1980 Vitellaro ............ F16L 11/24
156/170

(Continued)

FOREIGN PATENT DOCUMENTS

EP        1743672 A1 * 1/2007 ........... A61M 16/08
WO    WO 98/004310 A1    2/1998
(Continued)

OTHER PUBLICATIONS

"*Respiratory Physiology*", by John B. West, Lippincott Williams & Wilkins, $9^{th}$ edition published 2012 (8 pages).

(Continued)

*Primary Examiner* — Bradley H Philips
*Assistant Examiner* — Savannah L Gabriel
(74) *Attorney, Agent, or Firm* — Nixon & Vanderhye P.C.

(57) ABSTRACT

An air conduit for a respiratory therapy device comprises a first end, a second end, and a tube portion, wherein the tube portion comprises a tube wall and an auxiliary structure, such as a rib. The air conduit may deliver a flow of air from a respiratory therapy device or a humidifier to a patient interface. The air conduit may comprise a plurality of auxiliary structures, some of which may consist of a polymeric material, and some of which may comprise a polymeric material and an electrical conductor. An auxiliary structure may be a helical rib extending across a length of the tube portion.

27 Claims, 21 Drawing Sheets

(51) Int. Cl.
*A61M 16/16* (2006.01)
*A61M 16/06* (2006.01)
*A61M 16/00* (2006.01)

(52) U.S. Cl.
CPC .... *A61M 16/0875* (2013.01); *A61M 16/1095* (2014.02); *A61M 16/16* (2013.01); *A61M 16/0069* (2014.02); *A61M 16/107* (2014.02); *A61M 16/161* (2014.02); *A61M 2016/003* (2013.01); *A61M 2016/0033* (2013.01); *A61M 2205/3344* (2013.01); *A61M 2205/3368* (2013.01); *A61M 2205/3653* (2013.01)

(56) References Cited

U.S. PATENT DOCUMENTS

| | | | |
|---|---|---|---|
| 4,782,832 A | | 11/1988 | Trimble et al. |
| 4,944,310 A | | 7/1990 | Sullivan |
| 6,078,730 A | | 6/2000 | Huddart et al. |
| 6,367,510 B1 | | 4/2002 | Carlson |
| 6,532,959 B1 | | 3/2003 | Berthon-Jones |
| 6,581,594 B1 | | 6/2003 | Drew et al. |
| 7,866,944 B2 | | 1/2011 | Kenyon et al. |
| 8,078,040 B2 | * | 12/2011 | Forrester ................. F16L 11/12 392/481 |
| 8,636,479 B2 | | 1/2014 | Kenyon et al. |
| 8,638,014 B2 | | 1/2014 | Sears et al. |
| 8,733,349 B2 | | 5/2014 | Bath et al. |
| 8,936,047 B2 | * | 1/2015 | Hahn ..................... B29C 48/09 138/121 |
| 2009/0044808 A1 | | 2/2009 | Guney et al. |
| 2009/0050156 A1 | | 2/2009 | Ng et al. |
| 2009/0223514 A1 | | 9/2009 | Smith et al. |
| 2010/0000534 A1 | | 1/2010 | Kooij et al. |
| 2010/0083965 A1 | * | 4/2010 | Virr .................... A61M 16/109 128/203.26 |
| 2010/0215351 A1 | | 8/2010 | Forrester |
| 2013/0333701 A1 | | 12/2013 | Herron |
| 2014/0053939 A1 | * | 2/2014 | Kaye ................. A61M 16/0875 138/109 |
| 2014/0202462 A1 | * | 7/2014 | Stoks ................ A61M 16/0883 128/204.18 |
| 2015/0215351 A1 | * | 7/2015 | Barzuza ................ H04L 65/403 715/757 |
| 2015/0276097 A1 | * | 10/2015 | Carlson ................... F16L 11/04 156/143 |
| 2017/0049982 A1 | * | 2/2017 | Kavermann ...... A61M 16/0463 |
| 2017/0296769 A1 | * | 10/2017 | Smith ................... A61M 16/08 |

FOREIGN PATENT DOCUMENTS

| | | |
|---|---|---|
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2011/162622 A1 | 12/2011 |
| WO | WO 2012/171072 A1 | 12/2012 |
| WO | WO 2013/020167 A1 | 2/2013 |

OTHER PUBLICATIONS

International Search Report issued in PCT/AU2016/050942, dated Jan. 9, 2017, 5 pages.
Written Opinion of the ISA for PCT/AU2016/050942, dated Jan. 9, 2017, 6 pages.
International Preliminary Report on Patentability dated Apr. 10, 2018 issued in PCT/AU2016/050942 (7 pages).

* cited by examiner

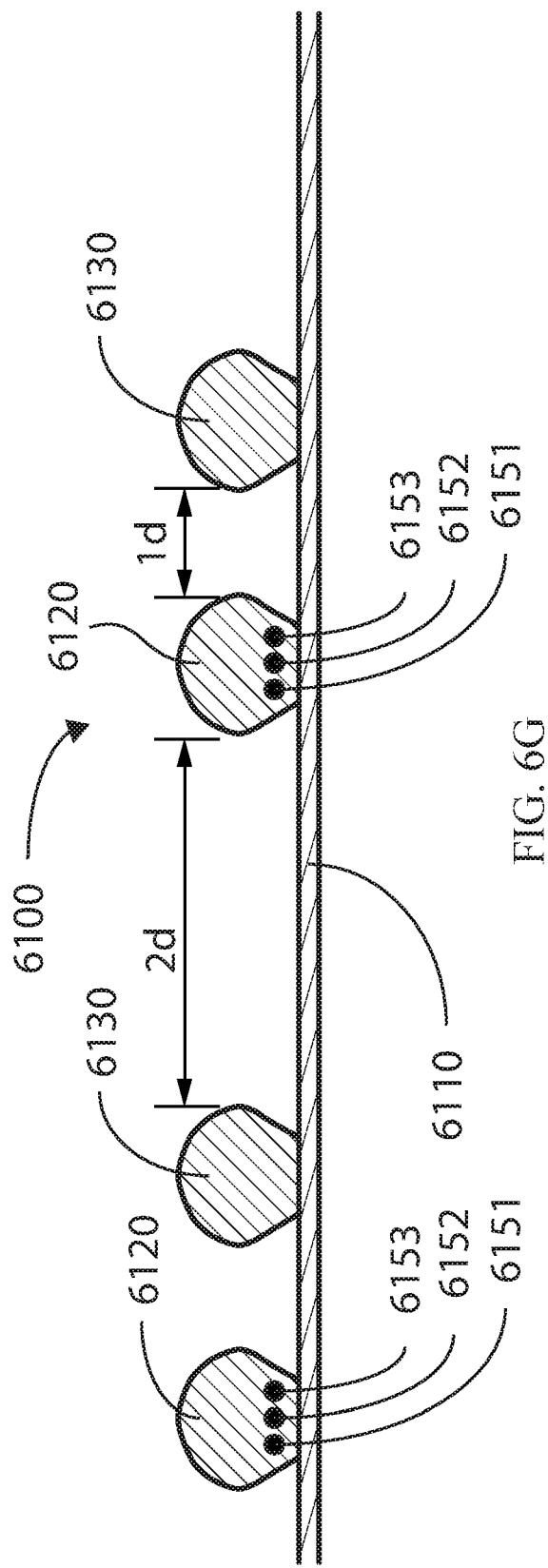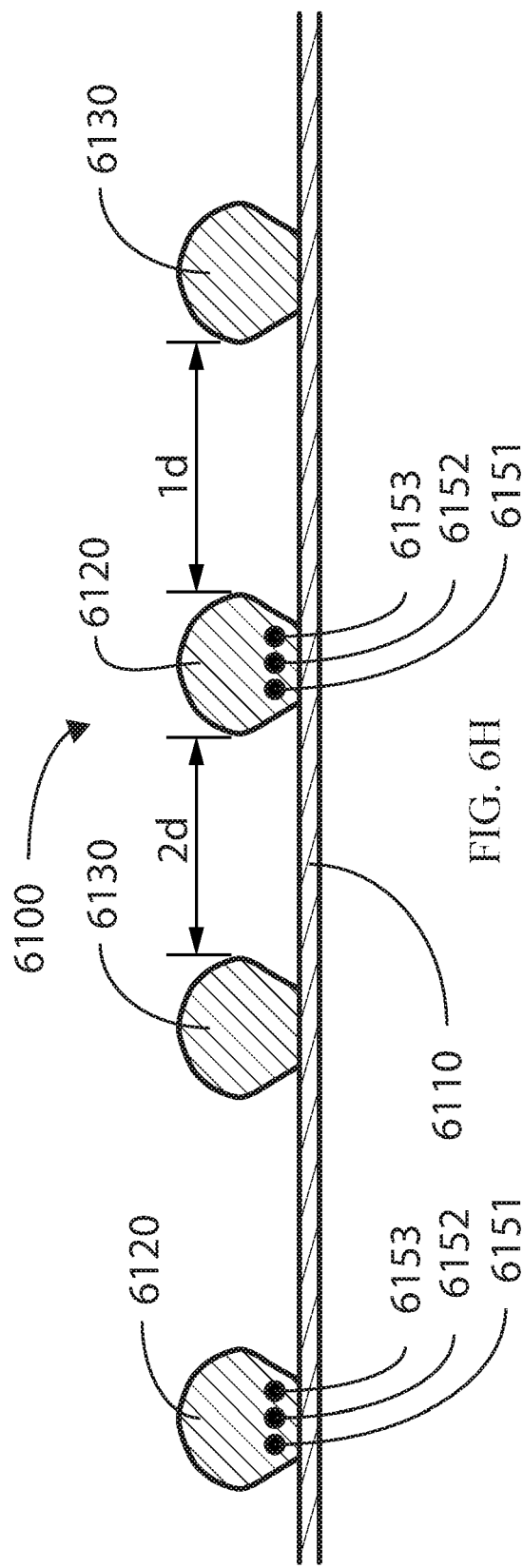

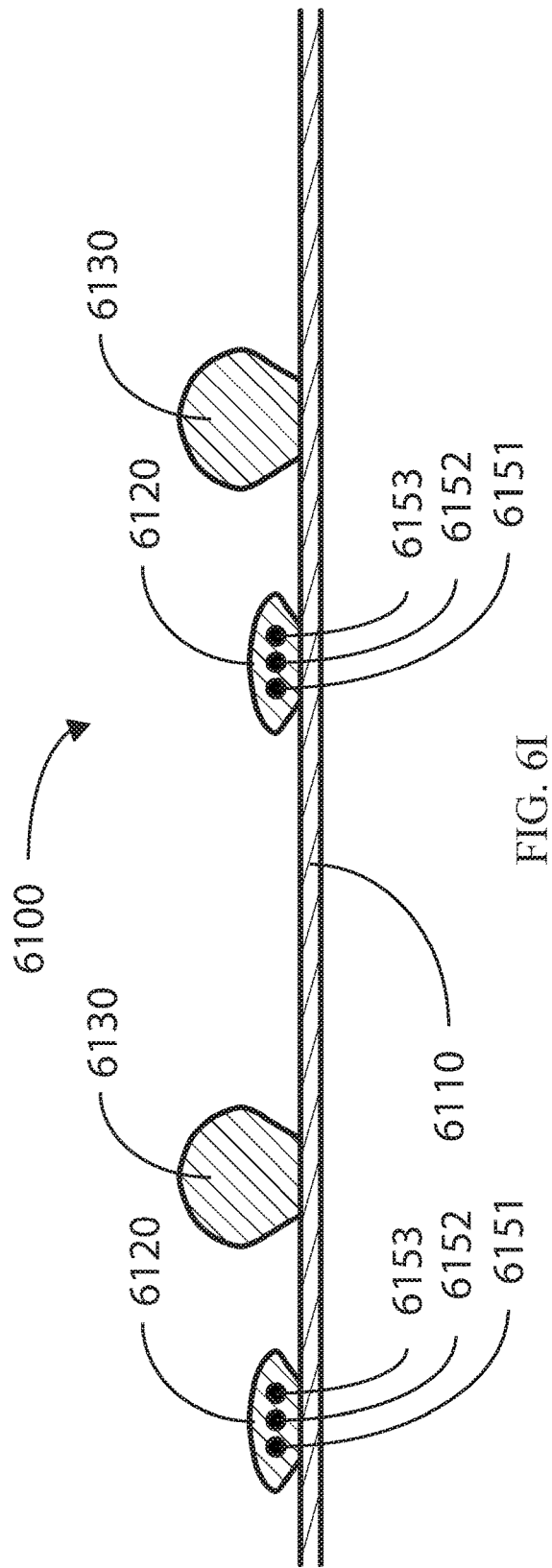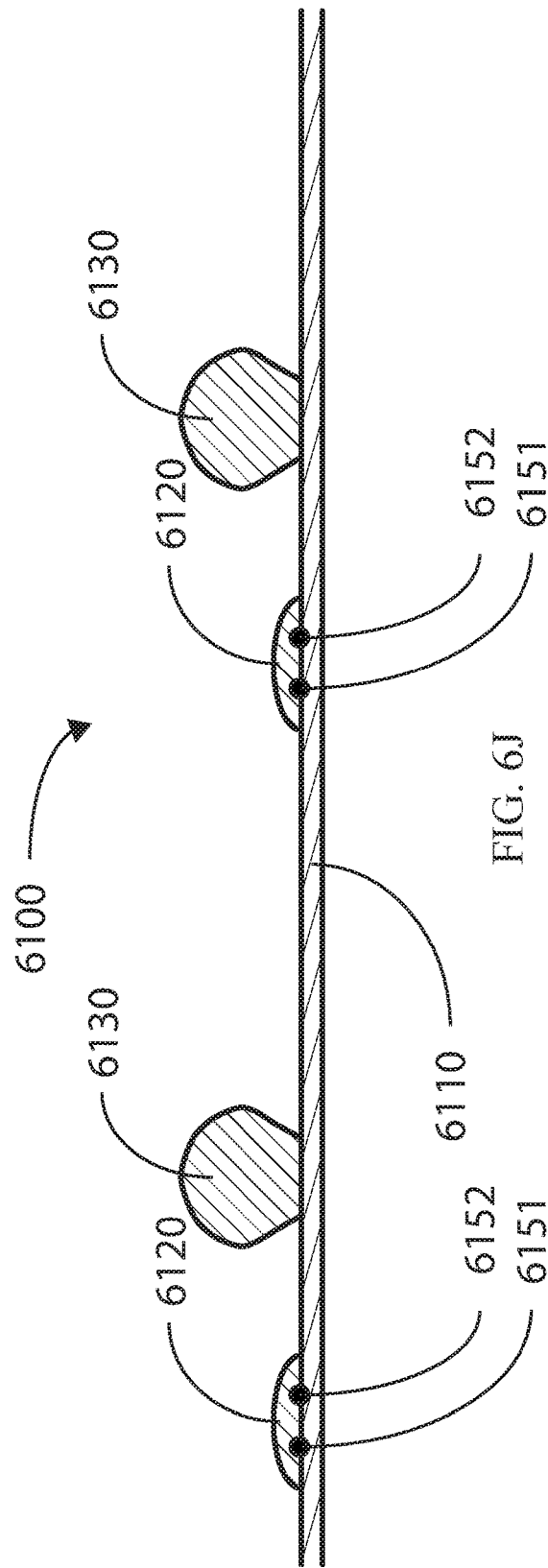

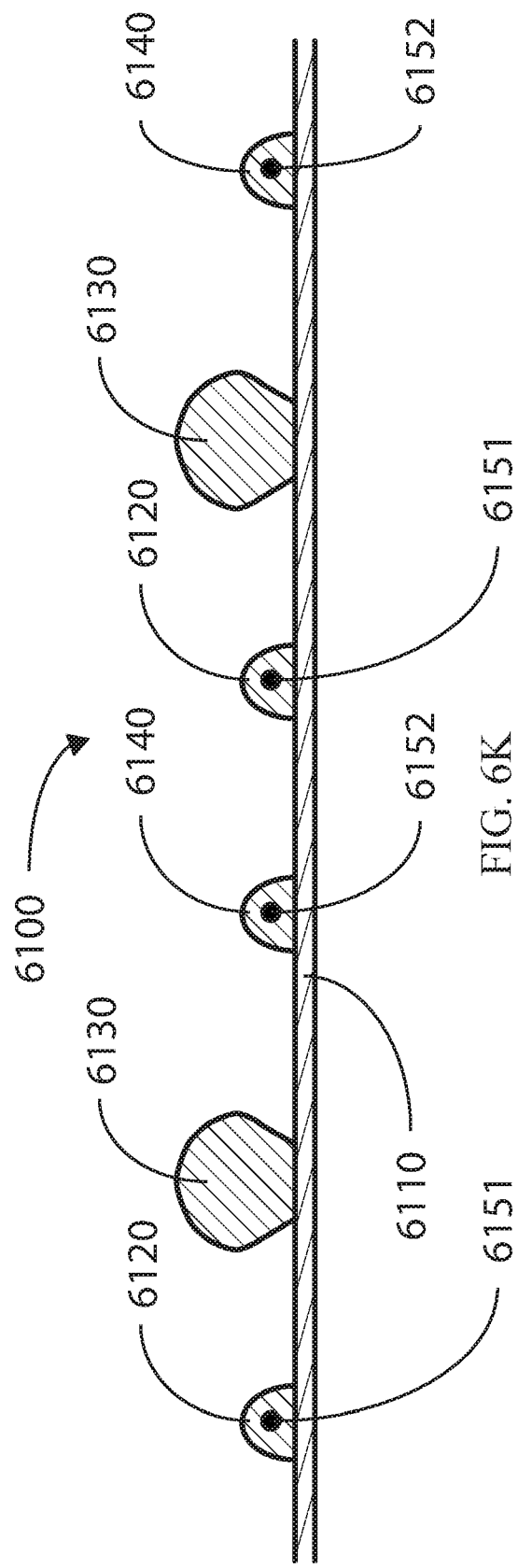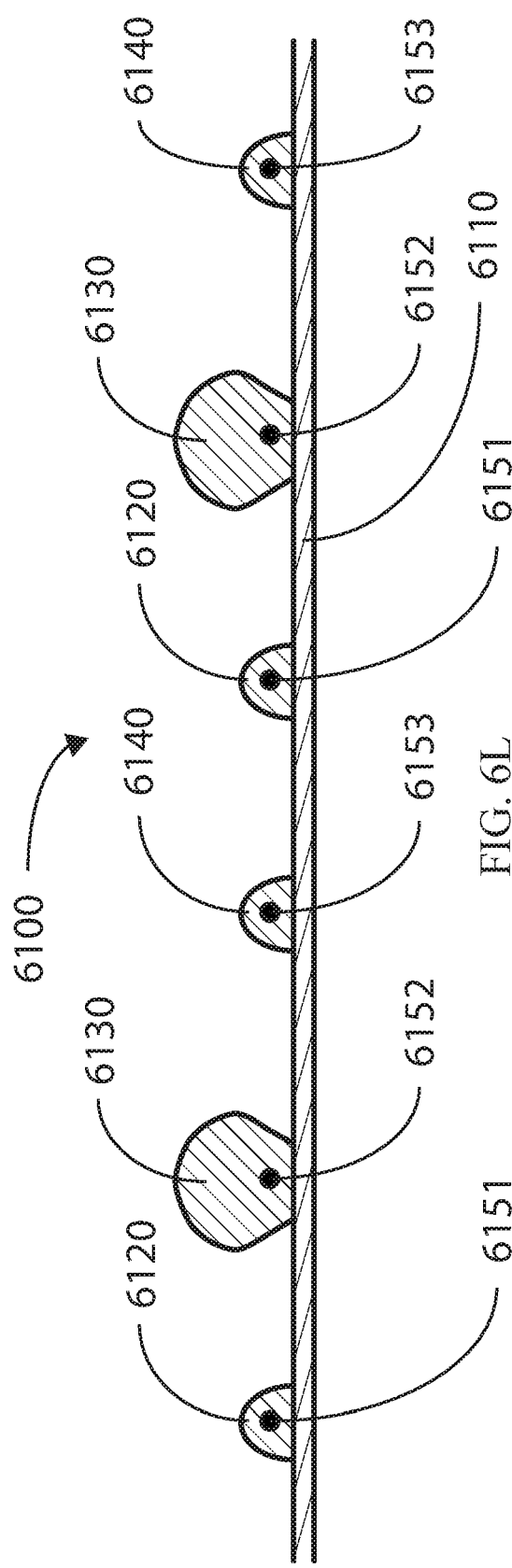
FIG. 6K
FIG. 6L

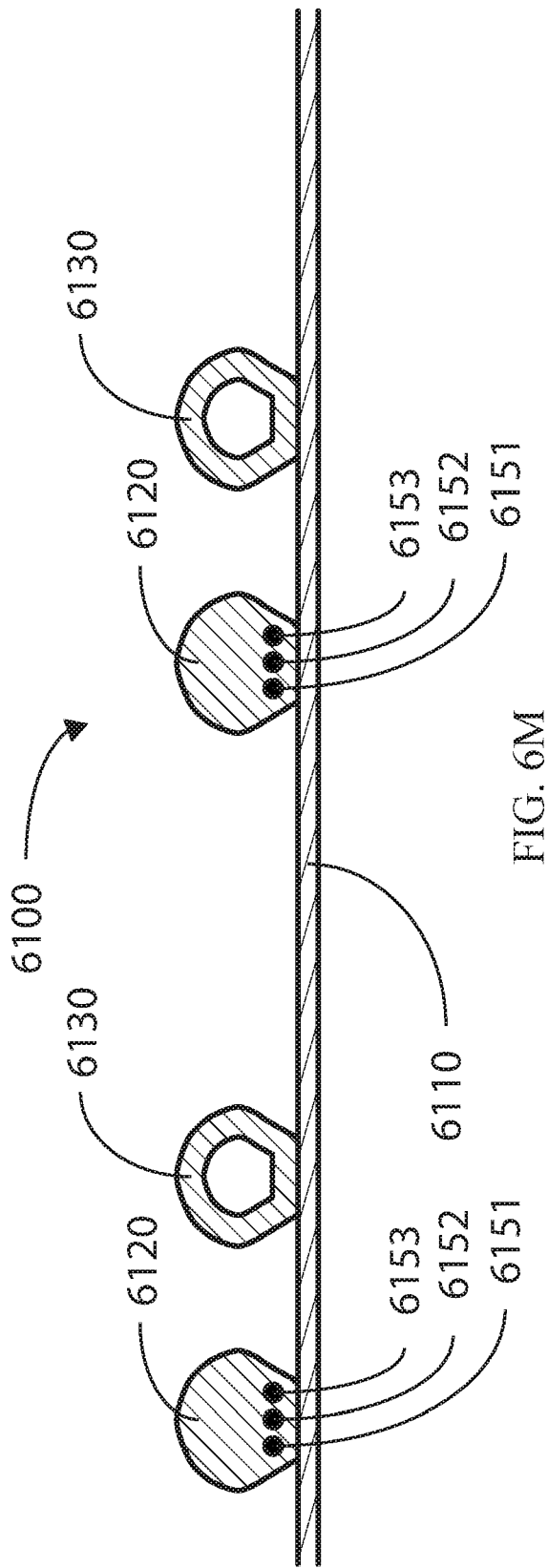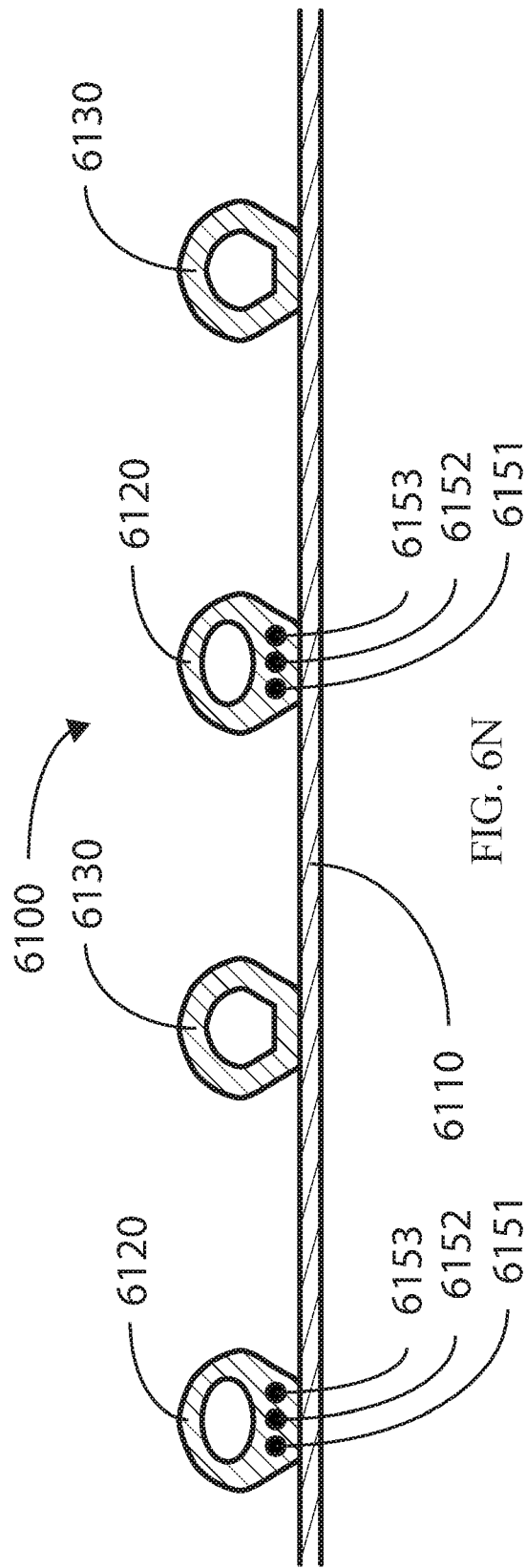

AIR CONDUIT FOR A RESPIRATORY DEVICE

1 CROSS-REFERENCE TO RELATED APPLICATIONS

This application is the U.S. national phase of International Application No. PCT/AU2016/050942 filed Oct. 7, 2016, which designated the U.S. and claims the benefit of Australian Provisional Application No. 2015904092, filed Oct. 8, 2015, the entire contents of each of which are incorporated herein by reference in its entirety.

2 BACKGROUND OF THE TECHNOLOGY

2.1 Field of the Technology

The present technology relates to medical devices or apparatus, and their use. More specifically, the present technology relates to an air conduit, such as one for delivering a flow of breathable gas.

2.2 Description of the Related Art

The respiratory system of the body facilitates gas exchange. The nose and mouth form the entrance to the airways of a patient.

A range of respiratory disorders exist. Certain disorders may be characterised by particular events, e.g., apneas, hypopneas, and hyperpneas.

A range of therapies have been used to treat or ameliorate such conditions. Furthermore, otherwise healthy individuals may take advantage of such therapies to prevent respiratory disorders from arising. However, these have a number of shortcomings.

Some examples of therapies are: Continuous Positive Airway Pressure (CPAP) therapy, Non-invasive ventilation (NIV) and Invasive ventilation (IV).

These therapies may be provided by a treatment system or device. Such systems and devices may also be used to diagnose a condition without treating it.

A treatment system may comprise a Respiratory Pressure Therapy Device (RPT device), an air conduit, a humidifier, a patient interface, and data management.

Air pressure generators are known in a range of applications, e.g., industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

One known RPT device used for treating sleep disordered breathing is the S9 Sleep Therapy System, manufactured by ResMed Limited. Another example of an RPT device is a ventilator.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device may be connected via an air conduit to a patient interface such as those described below.

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient.

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfill the specialised requirements of a medical humidifier.

Medical humidifiers are used to increase humidity and/or temperature of the flow of air in relation to ambient air when required, typically where the patient may be asleep or resting (e.g., at a hospital). A medical humidifier for bedside placement may be small. A medical humidifier may be configured to only humidify and/or heat the flow of air delivered to the patient without humidifying and/or heating the patient's surroundings. Room-based systems (e.g., a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

Some forms of treatment systems may include a vent to allow the washout of exhaled carbon dioxide. The vent may allow a flow of gas from an interior space of a patient interface to an exterior of the patient interface, e.g., to ambient. The vent may comprise an orifice and gas may flow through the orifice in use of the mask.

An air conduit is typically used to deliver a flow of air from a source to a destination. For example, an air conduit may deliver a flow of pressurised air from an outlet of an RPT device to an inlet of a humidifier. In another example, an air conduit may deliver a flow of pressurised air from an outlet of a humidifier to an inlet of a patient interface.

A number of different types of air conduits are known, which may be for example one or more of: heated and able to conduct electrical signals from one end to another end of the air conduit. To this end, air conduits exist that comprise electrical wires.

One example of air conduits in patent literature may be found in U.S. Pat. No. 8,733,349. U.S. Pat. No. 8,733,349 describe air conduits comprising one or more electrical wires, wherein the electrical wires may provide power and/or signalling functions to the air conduit. The electrical wires may be supported by the helical rib in contact with the outer surface of the air conduit.

Still, there exist a number of challenges in designing an air conduit that comprises electrical wires. Electrical wires may add to a size of the air conduit, making the final product less aesthetical appealing and/or less usable for the end user (e.g., patient or caregiver). Manufacture of electrical wires, particularly thin, high precision wires, may be costly, thus adding to the cost for the manufacturer and/or the consumer. Electrical wires are typically to be insulated for safety and reliability, and furthermore, the air conduit is preferably flexible globally such that deformation of the air conduit at one location does not lead to excessive forces at a second location of the air conduit, for example tending to displace a patient interface from the patient's face or move an RPT device from its intended location. As is the case with many design challenges, the designer/engineer faces numerous choices which may be beneficial in some ways but not others.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

One object of the present technology is to provide an air conduit which overcomes or mitigates one or more of the problems of the prior art, such as but not limited to those described above, or at least provides a useful alternative thereto.

An aspect of one form of the present technology is an air conduit for delivering a flow of air therethrough for respiratory therapy, the air conduit comprising a first end configured to form a pneumatic connection with a first respiratory apparatus to receive the flow of air, a second end configured to form a pneumatic connection with a second respiratory apparatus to deliver the flow of air from the first end, and a tube portion comprising a tube wall defining a path for the flow of air between the first end and the second end, a set of electrical conductors extending along a length of the tube portion, a first set of auxiliary structures extending along the length of the tube portion, and a second set of auxiliary structures extending along the length of the tube portion, wherein the first set of auxiliary structures comprises the set of electrical conductors, and the second set of auxiliary structures does not comprise an electrical conductor.

In another aspect of one form of the present technology, the first set of auxiliary structures helically extends along the length of the tube portion.

In another aspect of one form of the present technology, each of the second set of auxiliary structures comprises a larger cross section area than each of the first set of auxiliary structures.

In another aspect of one form of the present technology, each of the second set of auxiliary structures comprises a height exceeding 1 mm.

In another aspect of one form of the present technology, each of the first set of auxiliary structures comprises a height less than 1 mm.

In another aspect of one form of the present technology, the first set of auxiliary structures comprises the same pitch as the second set of auxiliary structures.

In another aspect of one form of the present technology, the first set of auxiliary structures consists of one auxiliary structure.

In another aspect of one form of the present technology, the second set of auxiliary structures consists of one auxiliary structure.

In another aspect of one form of the present technology, an auxiliary structure of the first set of auxiliary structures comprises a plurality of electrical conductors.

In another aspect of one form of the present technology, the set of electrical conductors comprises a copper wire.

In another aspect of one form of the present technology, the first end is further configured to electrically connect to the first respiratory apparatus.

In another aspect of one form of the present technology, the first end is configured to electrically connect the set of electrical conductors to the first respiratory apparatus.

In another aspect of one form of the present technology, the first respiratory apparatus is an RPT device or a humidifier.

In another aspect of one form of the present technology, the second respiratory apparatus is a patient interface.

An aspect of one form of the present technology is an air conduit for a respiratory apparatus, the air conduit comprising a first end comprising an electrical connector and a pneumatic connector, a second end comprising a pneumatic connector, and a tube portion configured to allow a flow of air between the first end and the second end, the tube portion comprising a wall defining a path for the flow of air between the first end and the second end, a first rib comprising of a first polymeric material and an electrical wire, wherein the electrical wire extends along the tube portion and is electrically connected to the electrical connector, and a second rib extending along the tube portion and consisting of a second polymeric material, wherein the electrical wire is configured to heat the flow of air and the second rib is configured to increase a rigidity of the tube portion.

In another aspect of one form of the present technology, the first rib is configured to increase a rigidity of the tube portion.

In another aspect of one form of the present technology, the first rib comprises a plurality of electrical wires.

In another aspect of one form of the present technology, the second rib extends helically along the tube portion.

In another aspect of one form of the present technology, the second rib comprises a solid cross section.

In another aspect of one form of the present technology, the electrical wire is further configured to transmit a signal therethrough.

In another aspect of one form of the present technology, the signal is generated by a sensor.

In another aspect of one form of the present technology, the sensor is in the second end.

In another aspect of one form of the present technology, the first polymeric material of the first rib is identical to the second polymeric material of the second rib.

In another aspect of one form of the present technology, the first polymeric material of the first rib is identical to the material of the tube wall.

An aspect of certain forms of the present technology is a medical device that is easy to use, e.g., by a person who does not have medical training, by a person who has limited dexterity, vision or by a person with limited experience in using this type of medical device.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

4.2 Respiratory System and Facial Anatomy

Figure 1A:
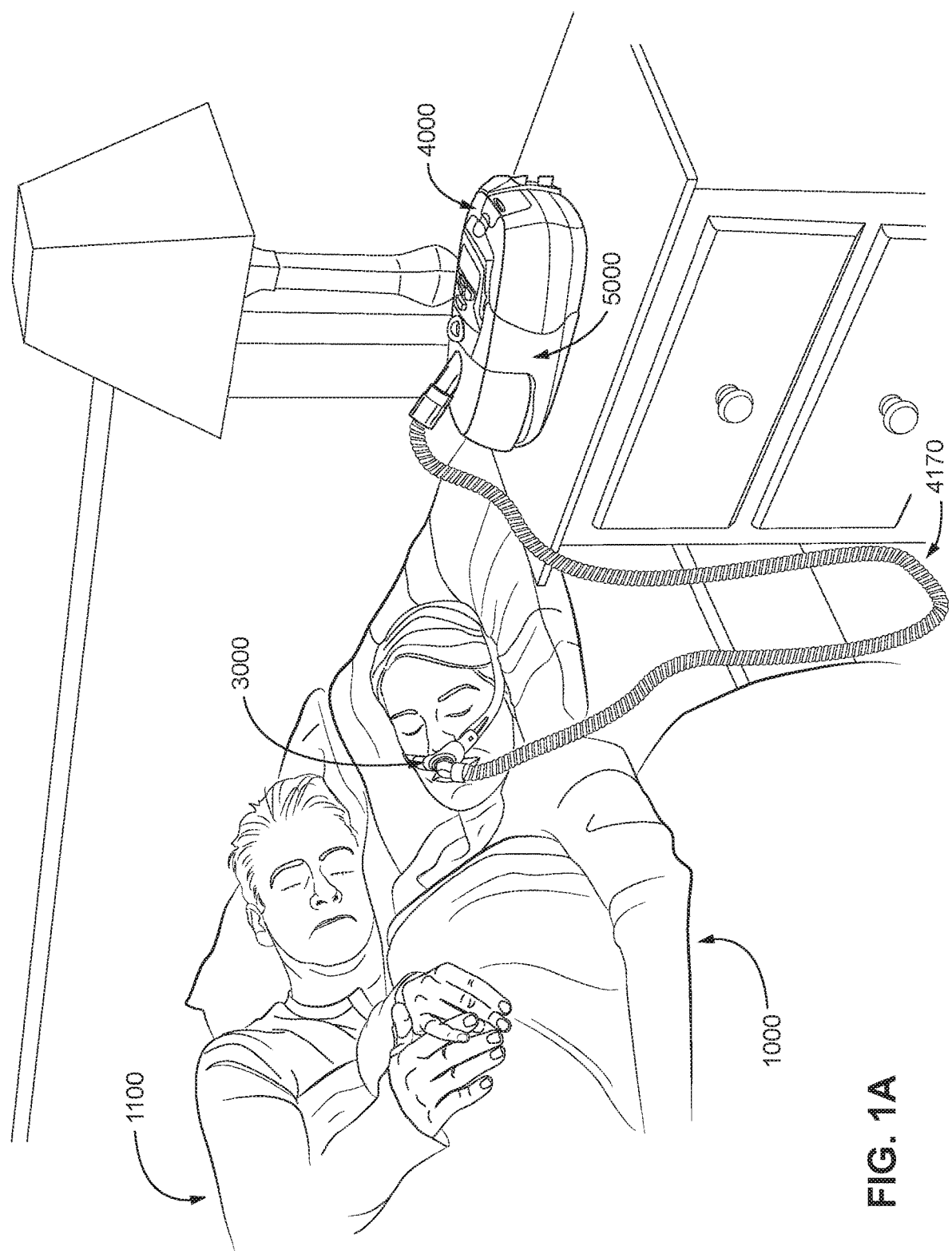
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
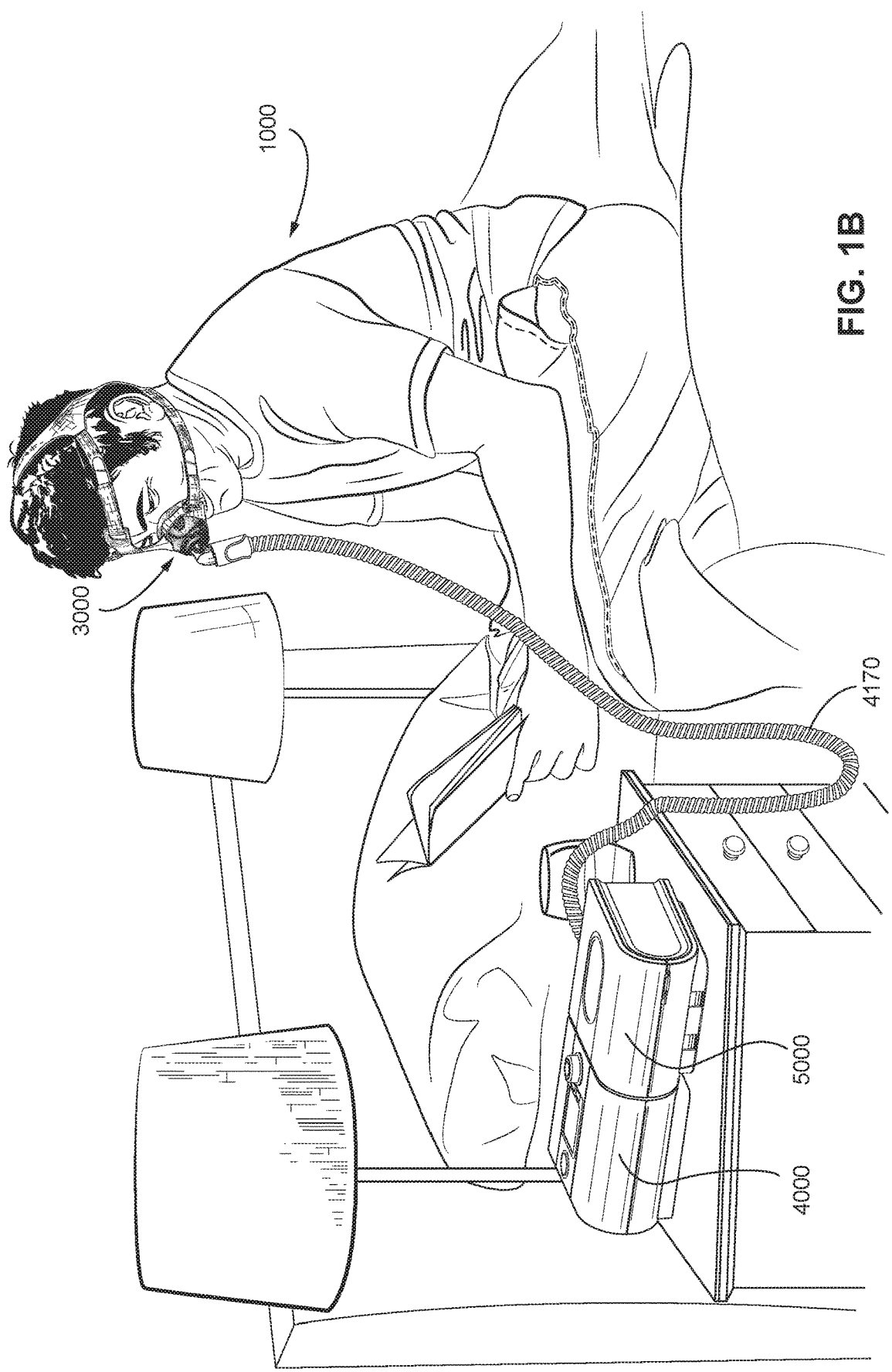
Figure 1C:
Figure 2A:
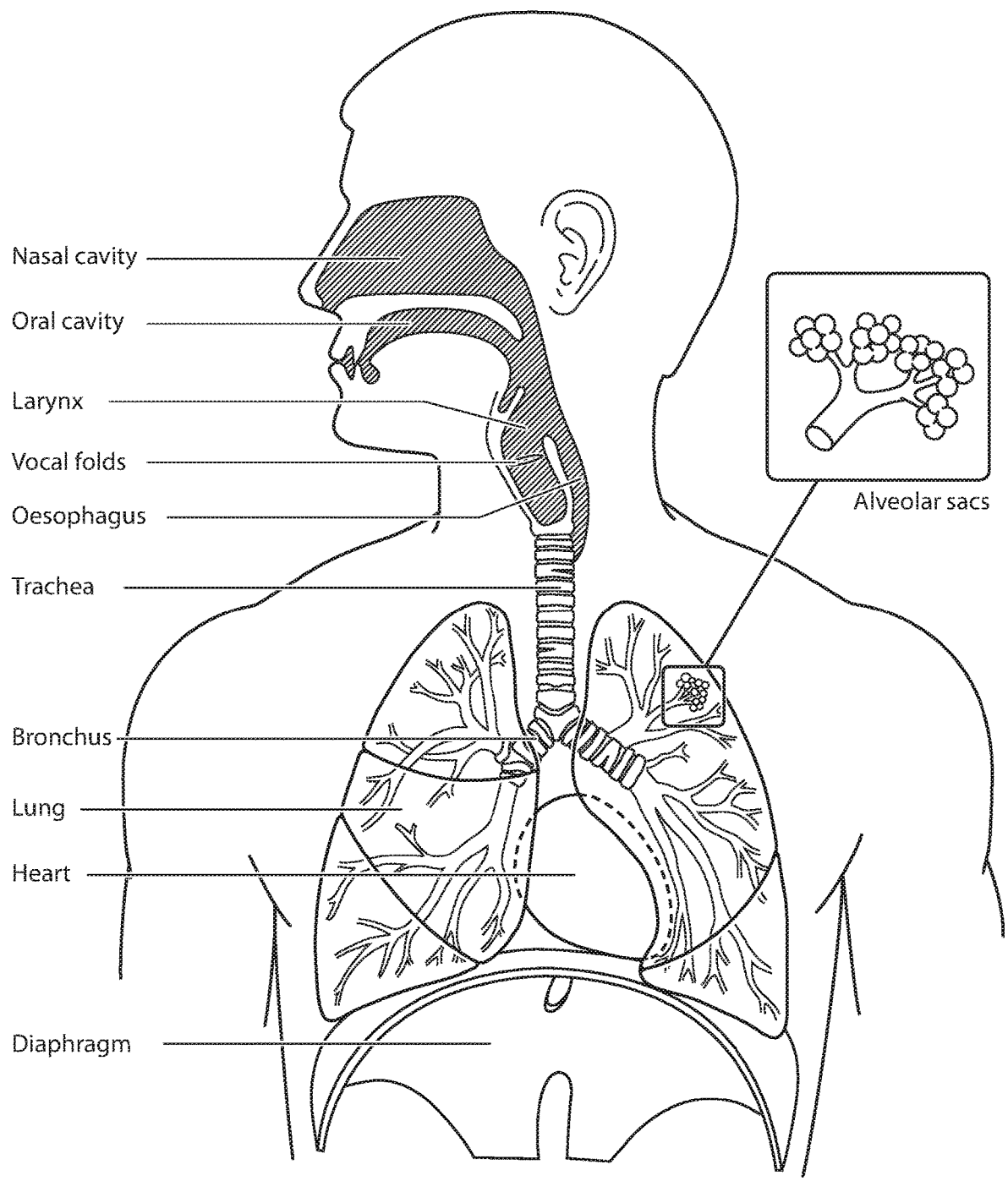

FIG. 2A shows an overview of a human respiratory system including the nasal and oral cavities, the larynx, vocal folds, oesophagus, trachea, bronchus, lung, alveolar sacs, heart and diaphragm.

Figure 2B:
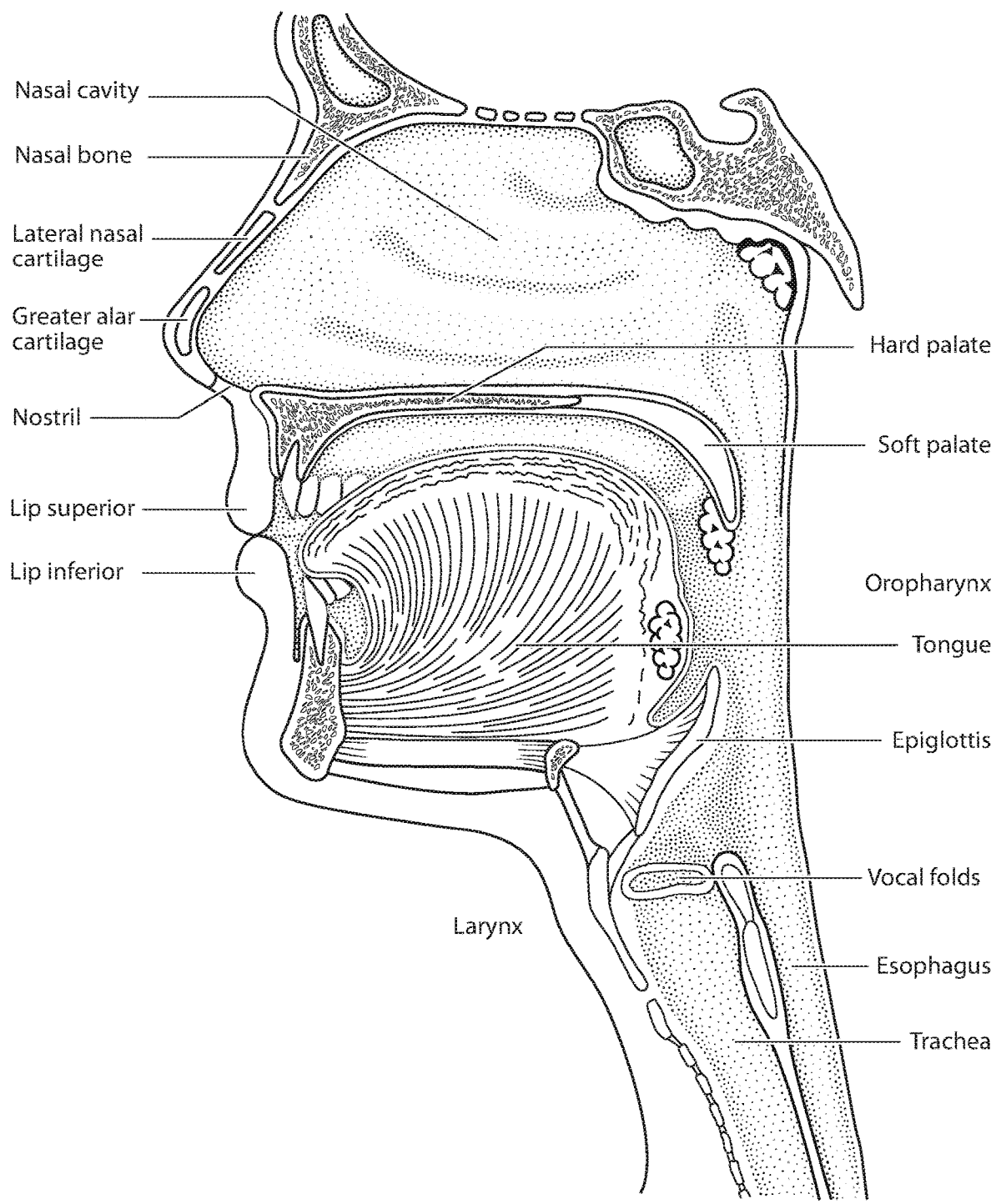

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.3 Patient Interface

Figure 3:
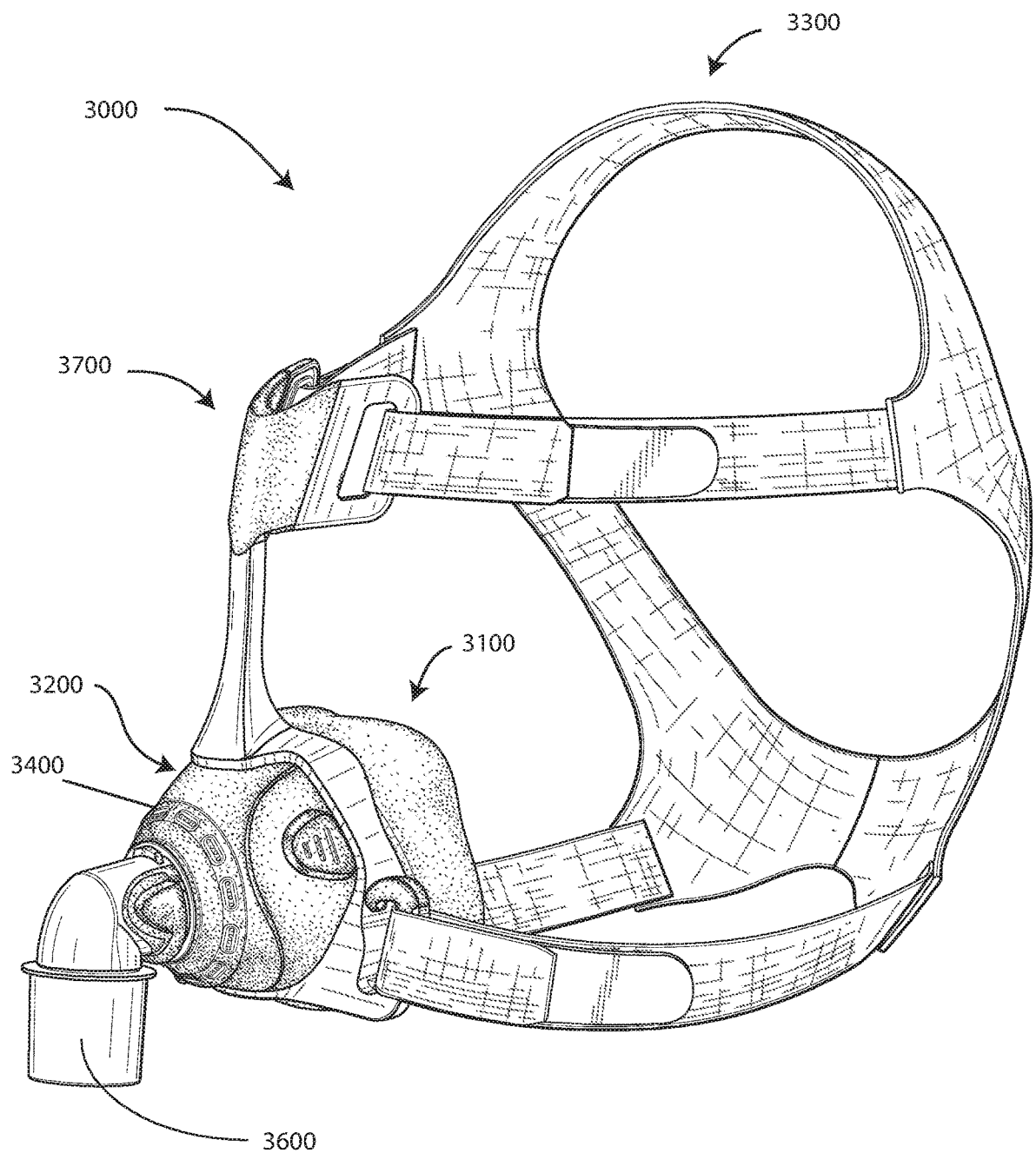

FIG. 3 shows a patient interface in the form of a nasal mask in accordance with one form of the present technology.

4.4 RPT Device

Figure 4A:
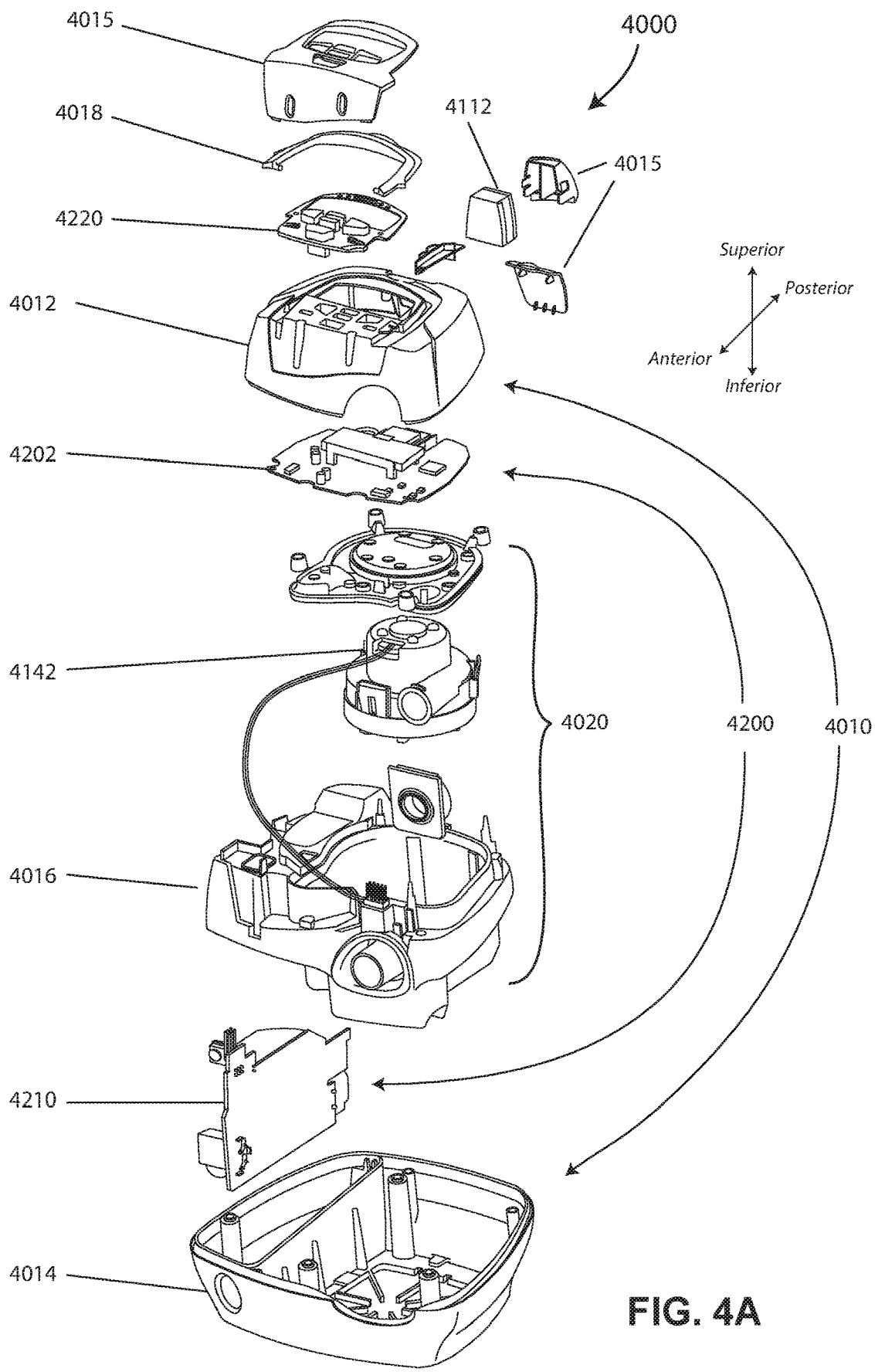

FIG. 4A shows an RPT device in accordance with one form of the present technology.

Figure 4B:
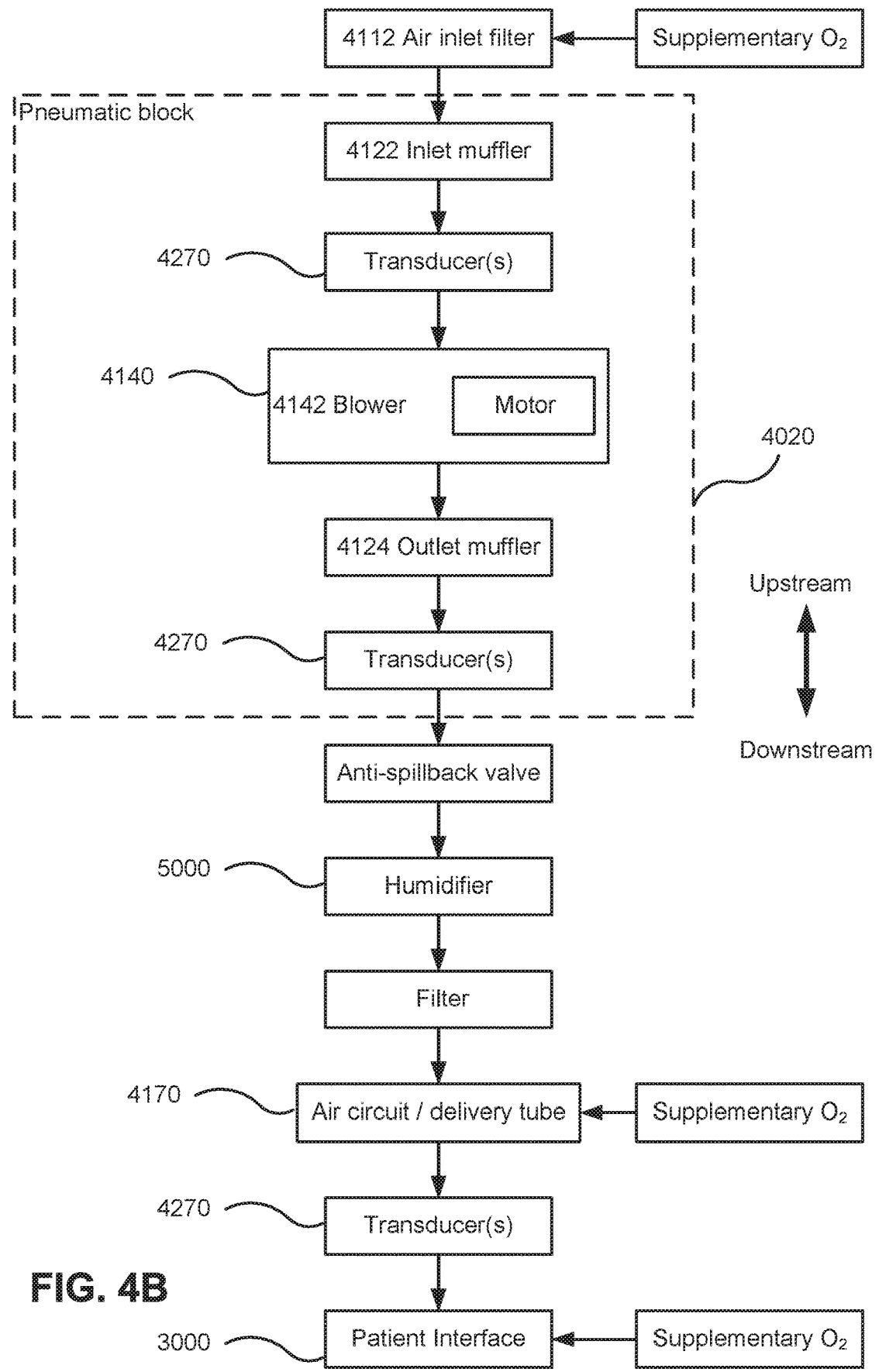

FIG. 4B is a schematic diagram of the pneumatic path of an RPT device in accordance with one form of the present technology. The directions of upstream and downstream are indicated.

Figure 4C:
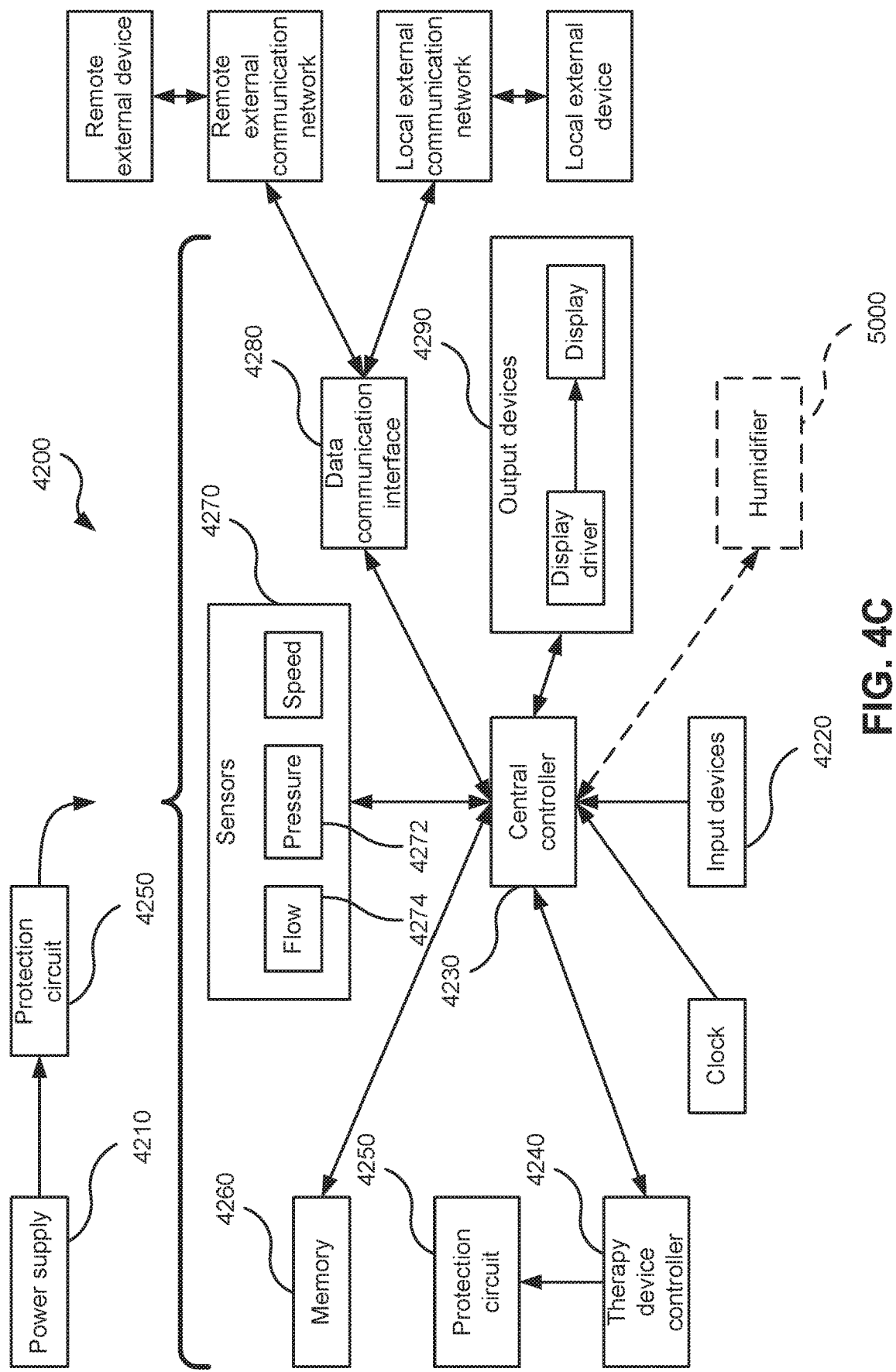

FIG. 4C is a schematic diagram of the electrical components of an RPT device in accordance with one form of the present technology.

Figure 4D:
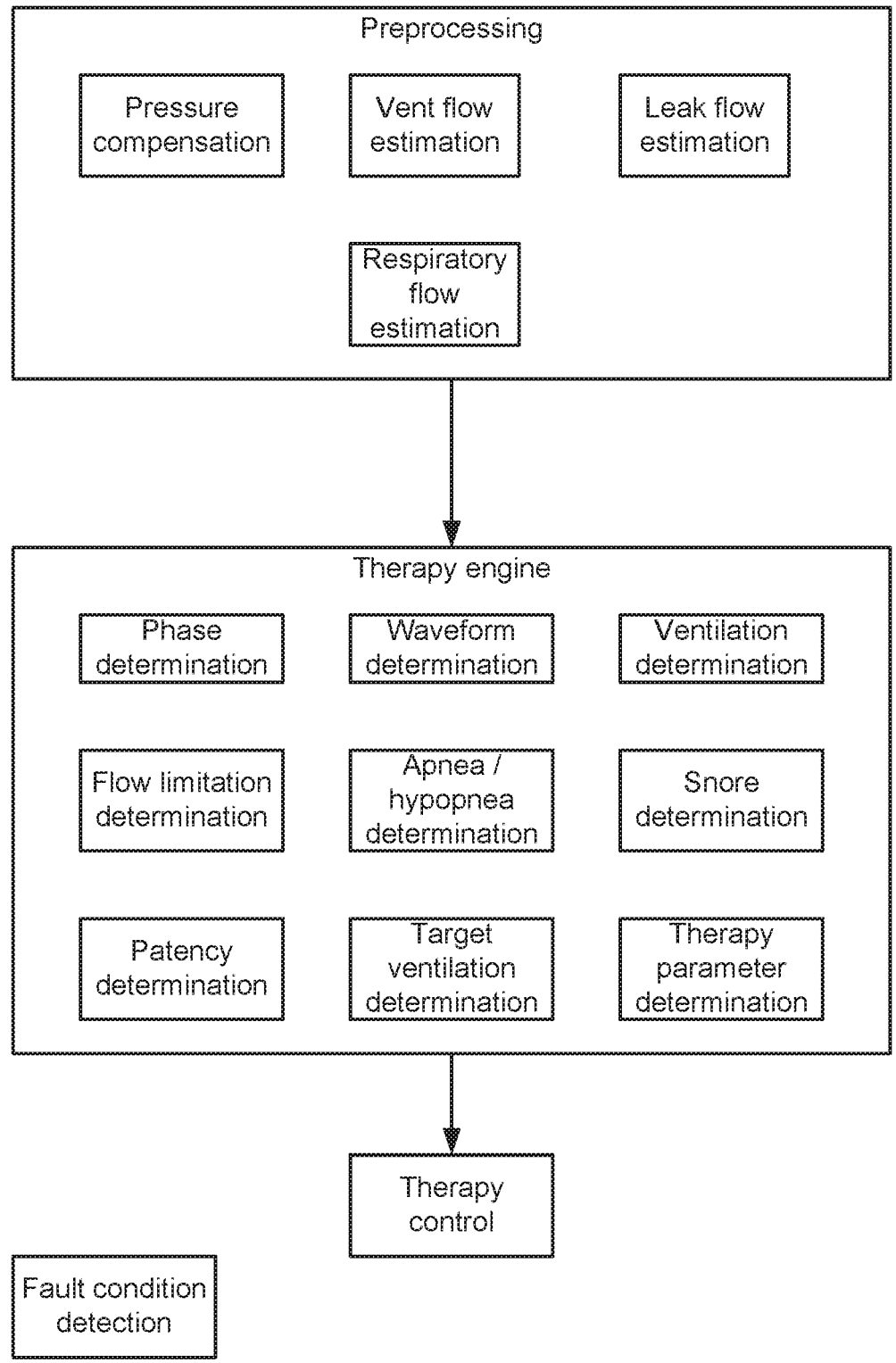

FIG. 4D is a schematic diagram of the algorithms implemented in an RPT device in accordance with one form of the present technology.

4.5 Humidifier

Figure 5A:
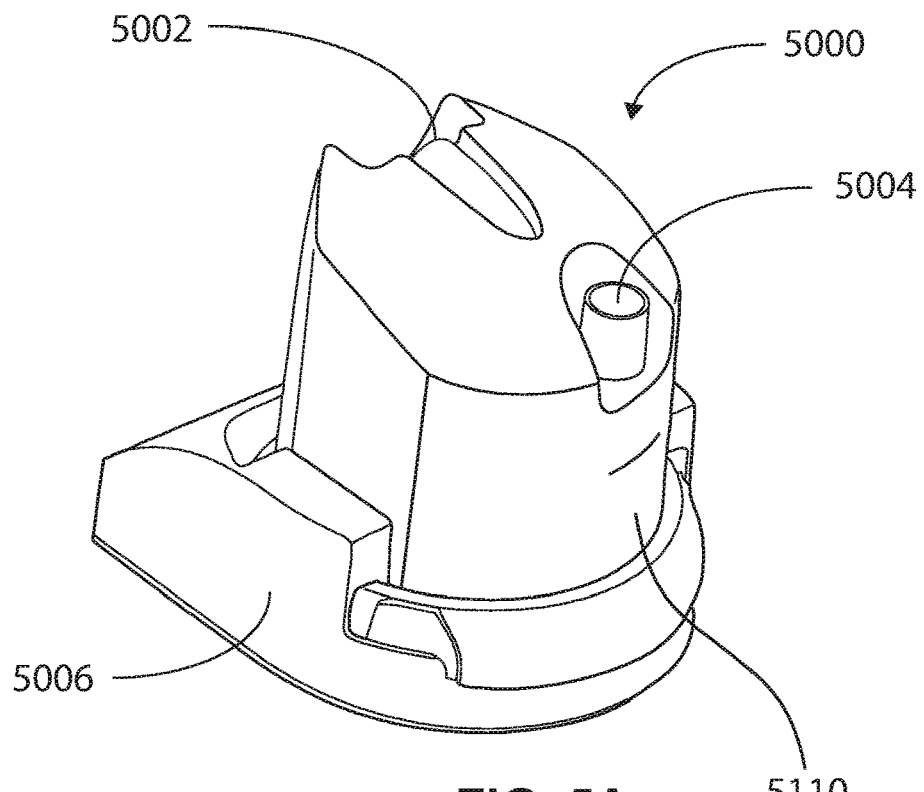

FIG. 5A shows an isometric view of a humidifier in accordance with one form of the present technology.

Figure 5B:
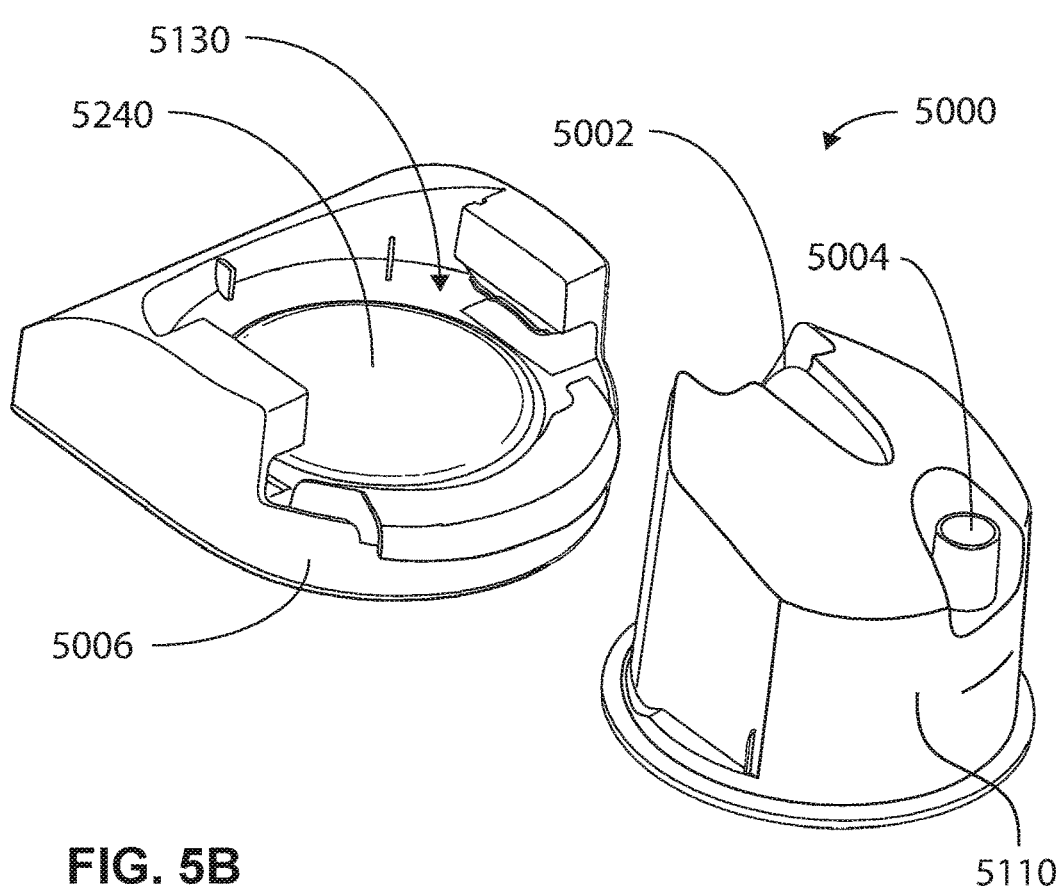

FIG. 5B shows an isometric view of a humidifier in accordance with one form of the present technology, showing a humidifier reservoir 5110 removed from the humidifier reservoir dock 5130.

Figure 5C:
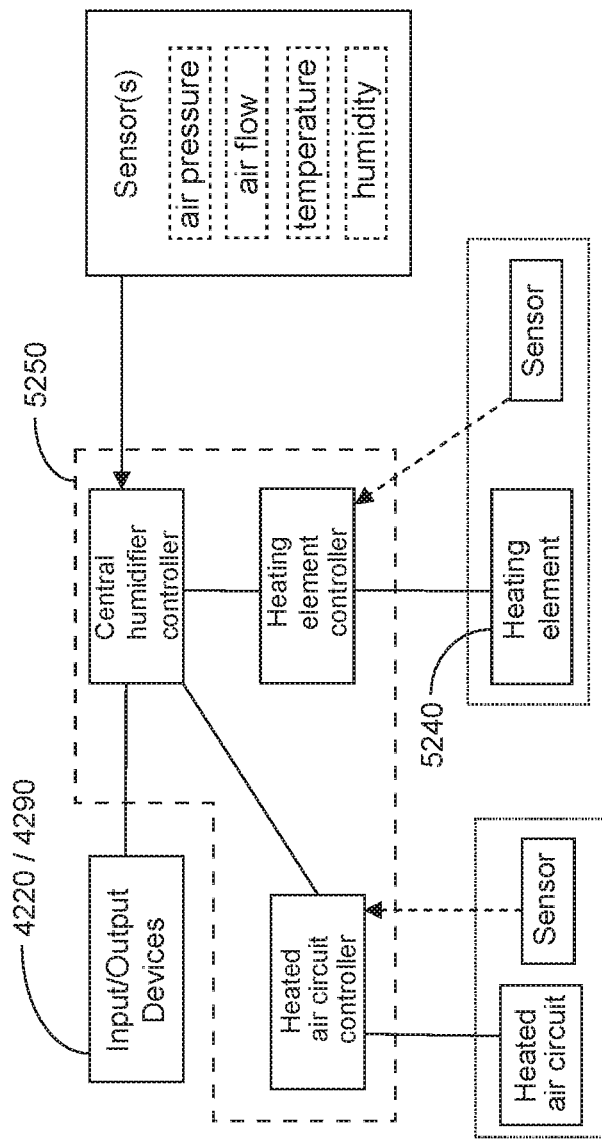

FIG. 5C shows a schematic of a humidifier in accordance with one form of the present technology.

4.6 Air Conduit

Figure 6A:
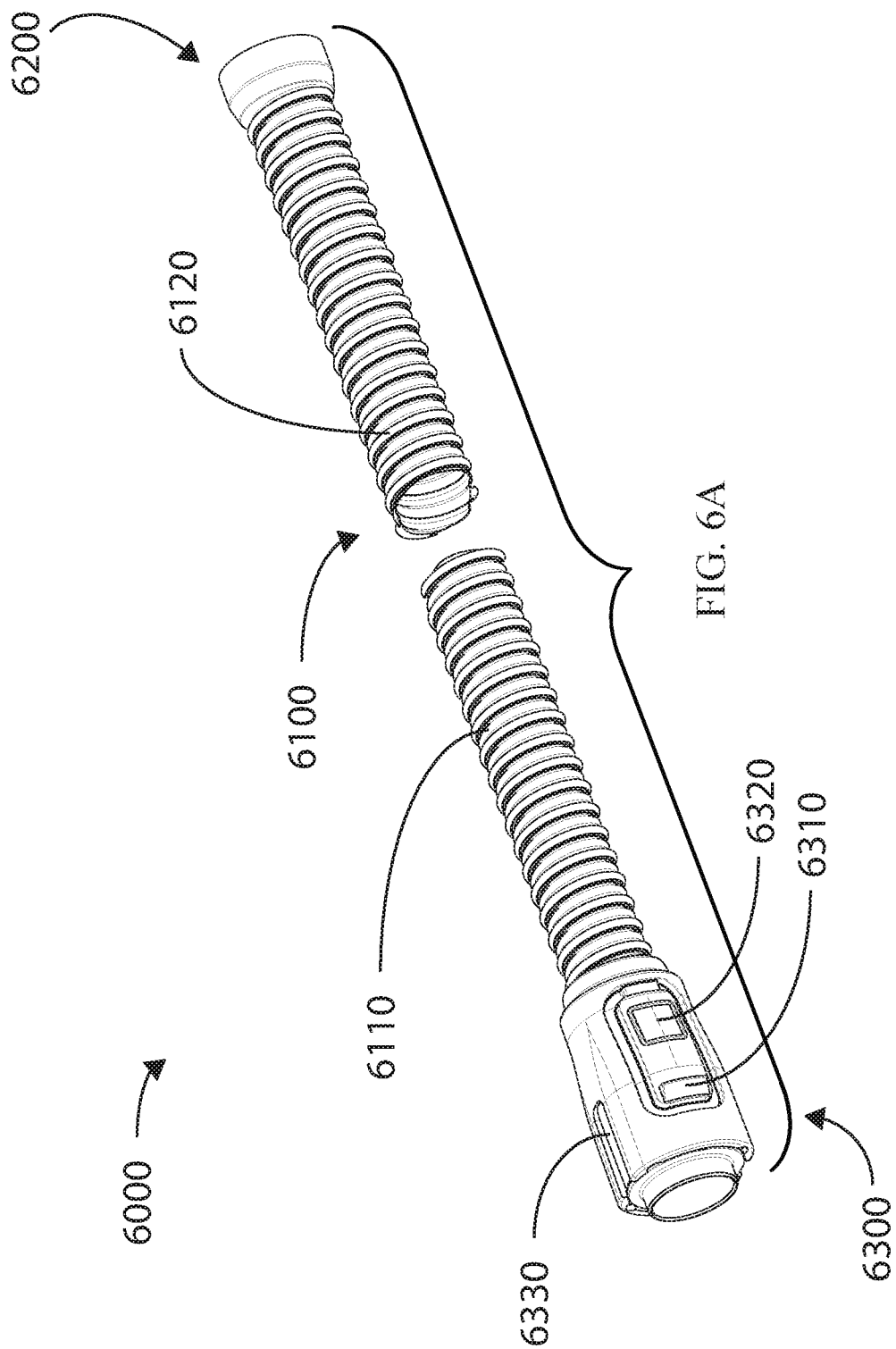

FIG. 6A shows an isometric view of an air conduit in accordance with one form of the present technology.

Figure 6B:
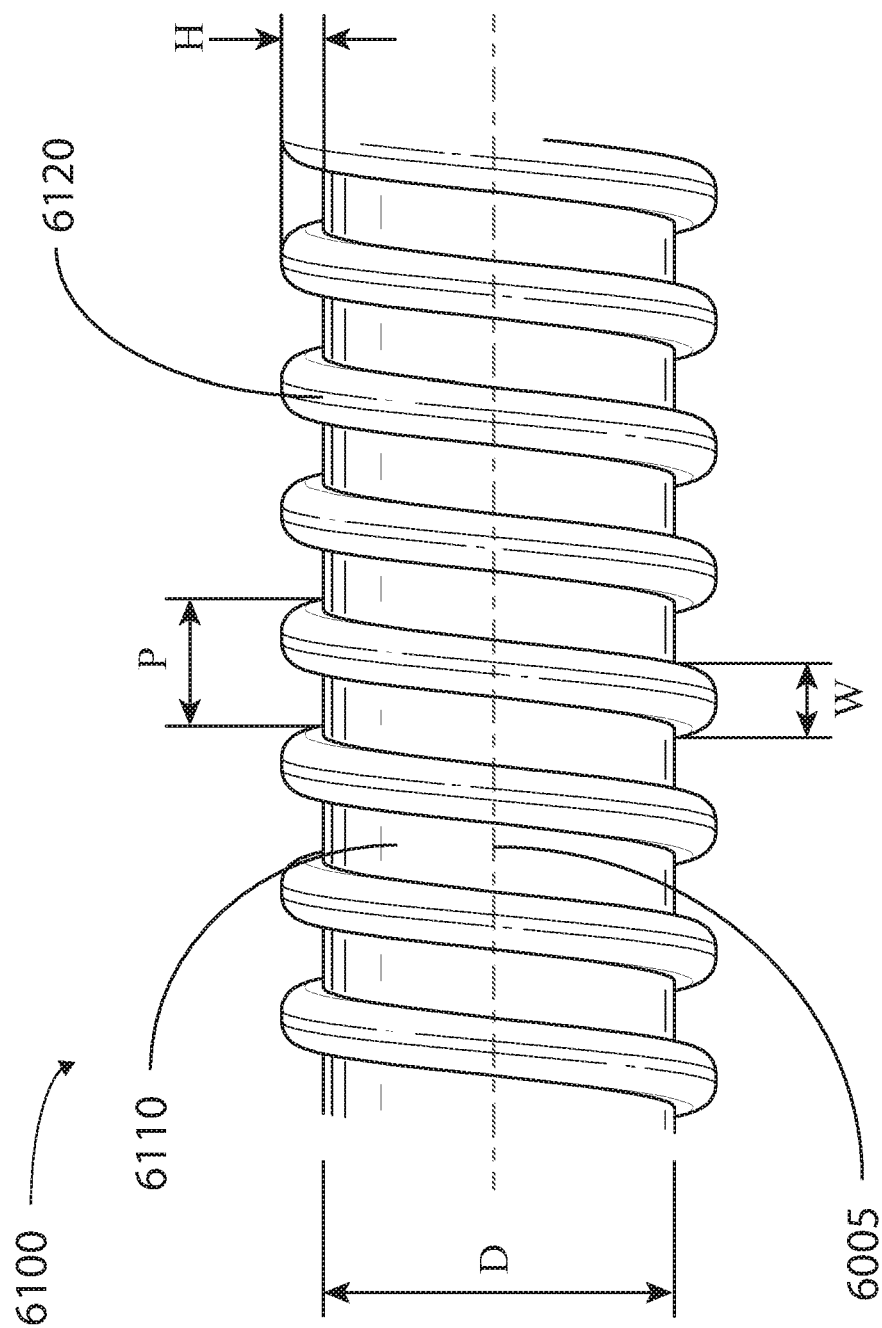

FIG. 6B shows a partial view of a tube portion of air conduit in accordance with one form of the present technology.

Figure 6C:
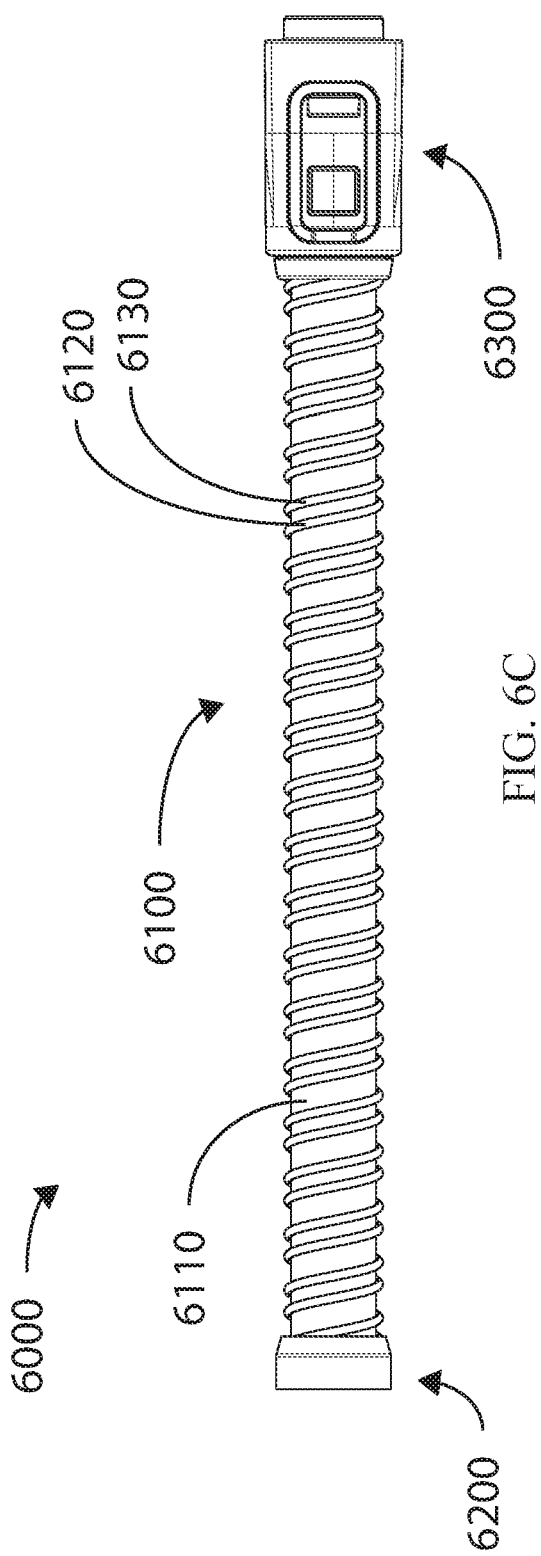

FIG. 6C shows a plan view of an air conduit in accordance with one form of the present technology.

Figure 6D:
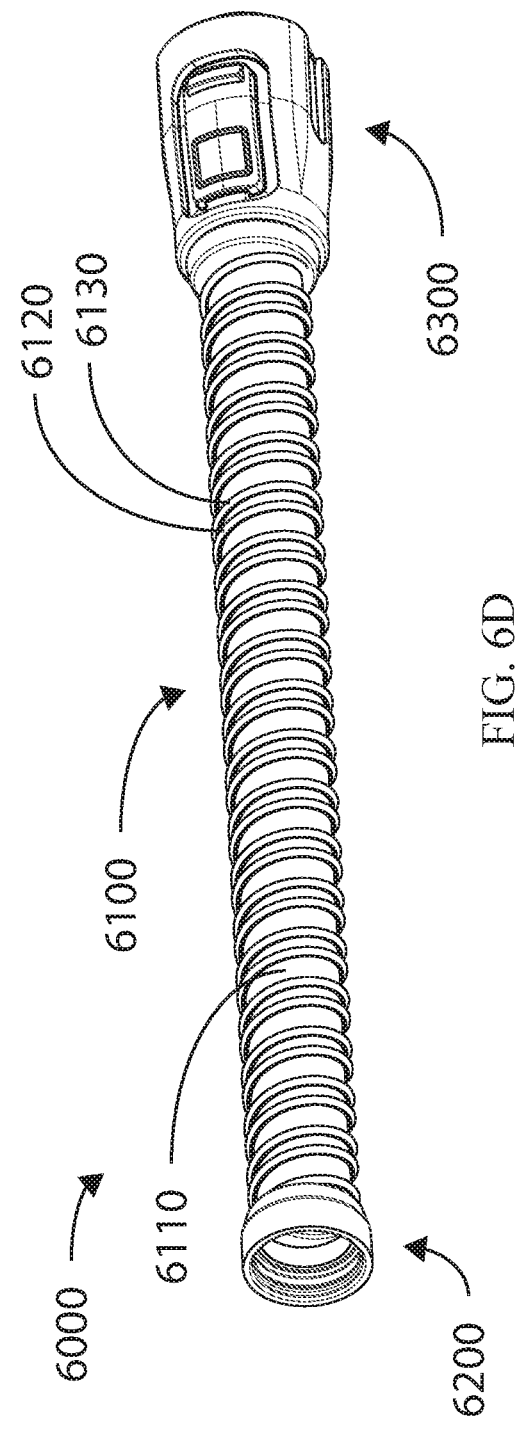

FIG. 6D shows an isometric view of an air conduit in accordance with one form of the present technology.

Figure 6E:
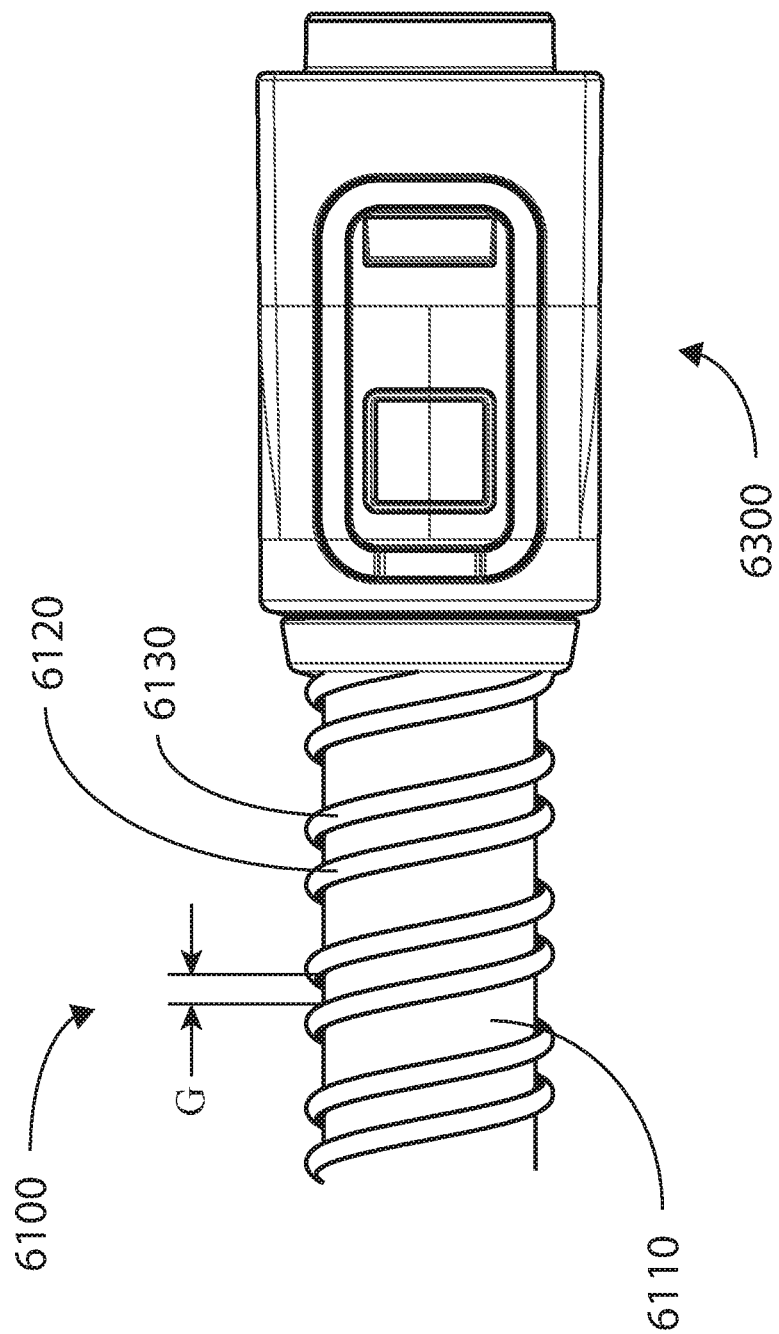

FIG. 6E shows a plan view of a portion of an air conduit in accordance with one form of the present technology.

Figure 6F:
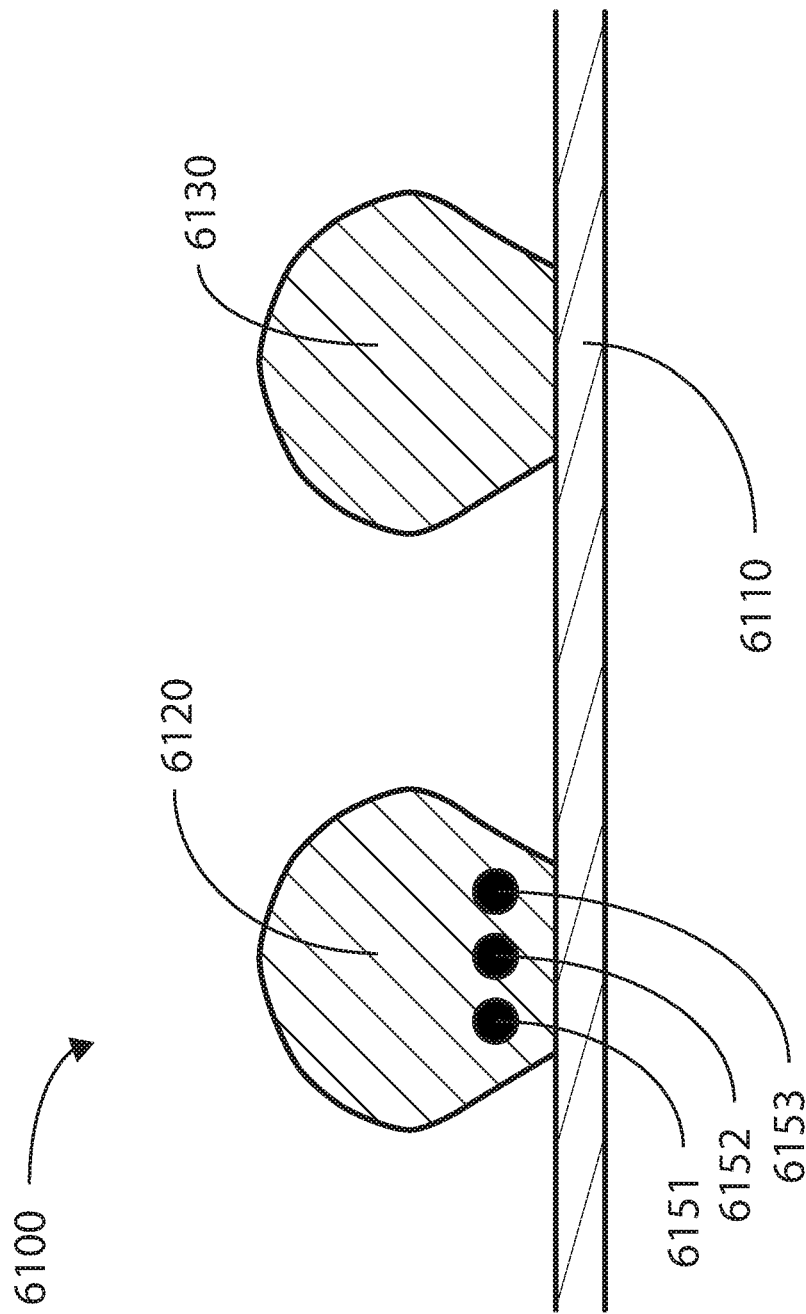

FIG. 6F shows a cross section view of a tube portion of an air conduit in accordance with one form of the present technology.

FIG. 6G shows a cross section view of a tube portion of an air conduit in accordance with one form of the present technology.

FIG. 6H shows a cross section view of a tube portion of an air conduit in accordance with one form of the present technology.

FIG. 6I shows a cross section view of a tube portion of an air conduit in accordance with one form of the present technology.

FIG. 6J shows a cross section view of a tube portion of an air conduit in accordance with one form of the present technology.

FIG. 6K shows a cross section view of a tube portion of an air conduit in accordance with one form of the present technology.

FIG. 6L shows a cross section view of a tube portion of an air conduit in accordance with one form of the present technology.

FIG. 6M shows a cross section view of a tube portion of an air conduit in accordance with one form of the present technology.

FIG. 6N shows a cross section view of a tube portion of an air conduit in accordance with one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Treatment Systems

In one form, the present technology comprises an apparatus or device for treating a respiratory disorder. The apparatus or device may comprise an RPT device 4000 for supplying pressurised air to the patient 1000 via an air conduit 6000 (e.g., as shown in FIGS. 6A to 6N) to a patient interface 3000.

5.2 Patient Interface

As shown in FIG. 3, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air conduit 6000, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3 Vent

A treatment system may include a vent 3400 constructed and arranged to allow for the washout of exhaled gases, e.g. carbon dioxide. In one form, the patient interface 3000 may comprise a vent 3400.

5.4 RPT Device

As shown in FIG. 4A to 4C, an RPT device 4000 in accordance with one aspect of the present technology comprises mechanical and pneumatic components, electrical components and is configured to execute one or more algorithms 4300 (e.g., see FIG. 4D). The RPT device may have an external housing 4010, for example formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

5.4.1.1 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

The central controller 4230 may be configured to receive input signal(s) from one or more transducers, as a sensor located on the air conduit 6000, one or more input devices 4220, and the humidifier 5000.

The central controller 4230 may be configured to provide output signal(s) to one or more of an output device 4290, a therapy device controller 4240, a data communication interface 4280, and the humidifier 5000.

5.5 Humidifier

In one form of the present technology there is provided a humidifier 5000 (e.g., as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

Thus, a humidifier 5000 may deliver from its outlet 5004 a humidified flow of air. The humidified flow of air may have an increased absolute humidity and/or temperature in comparison to the ambient as described elsewhere in the present document.

5.5.1.1 Humidifier Controller

According to one arrangement of the present technology, as shown in FIG. 5C, a humidifier 5000 may comprise a humidifier controller 5250. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

5.6 Air Conduit

FIGS. 6A to 6N show an air conduit 6000 in accordance with an aspect of the present technology that is constructed and arranged to allow a flow of air to travel therethrough. For example, the air conduit 6000 may, in use, allow a flow of air to travel between two components such as the pneumatic block 4020 and the patient interface 3000. The air conduit 6000, in combination with one or more of the pneumatic block 4020 and the patient interface 3000, may form an air circuit.

The air conduit 6000 may be configured to be connectable to an outlet of the pneumatic block 4020 (e.g., an outlet of the RPT device 3000) at a first end and an inlet of the patient interface 3000 (e.g., a connection port 3600) at a second end. The air conduit may be referred to as an air tube or an air delivery tube. In some cases, there may be separate limbs of the air circuit for inhalation and exhalation. In other cases, a single limb may be used.

The flow of air travelling through the air conduit 6000 may pressurized, such as at a pressure of between 2 cm $H_2O$ and 30 cm $H_2O$, or depending on therapy requirements. In some forms, the flow of air may be humidified, such as to a relative humidity of up to 90%, 95% or 100%. In some forms, the flow of air may be at a different (e.g., higher) temperature to the surrounding air, such as at 30 degrees Celsius, while the ambient temperature is approximately 20 degrees Celsius.

Thus, the air conduit 6000 may be configured and arranged to support the pressure, temperature and/or humidity of the flow of air travelling therethrough. In some forms, the air conduit 6000 may comprise one or more heating elements configured to heat air in the air conduit, e.g., to maintain or raise the temperature of the air.

Also, as a medical device, the air conduit 6000 may be configured and arranged to minimise build-up of undesirable contaminants therein, such as to meet bioburden requirements for safe usage.

Still further, the air conduit 6000 is preferably configured such that its usage does not adversely affect a performance of an apparatus that it operates with, such as a patient interface 3000, an RPT device 4000 and/or a humidifier 5000. For example, an air conduit 6000 comprising a high bending stiffness may be more likely to displace a patient interface 3000, an RPT device 4000 or a humidifier 5000 in comparison to an air conduit 6000 comprising a lower bending stiffness. Such a displacement may adversely affect a pressure and/or a flow rate delivered by the patient interface 3000 or disrupt operation of the RPT device 4000 or a humidifier 5000, e.g., be tipped over, or worse, become disconnected, e.g., at a power source. This could be potentially dangerous in situations where a patient is immobile and potentially could be relying on the respiratory therapy system to breathe. Thus, the air conduit 6000 may preferably comprise a low bending stiffness.

Yet, on the other hand, the air conduit 6000 is preferably locally stiff to prevent occlusion, such as from deformation. To effectively and predictably deliver a flow of air to the patient, the air conduit 6000 is substantially patent without deformation to its conduit cross section. An occlusion to the air conduit 6000, such as to reduce its cross section area by 50% or more, could lead to a significantly increased resistance to air flow therethrough, which may in turn adversely affect a flow rate and/or pressure of the air delivered to the patient.

For at least the above reasons, air conduits for use in a respiratory therapy system, such as with a patient interface 3000, an RPT device 4000 and/or a humidifier 5000 may form its own distinct field.

An exemplary single limb air conduit 6000 is shown in FIG. 6A. The air conduit 6000 of FIG. 6A comprises first end 6200, second end 6300, and tube portion 6100 fluidly connecting the first end 6200 to the second end 6300. The tube portion 6100 may comprise a tube wall 6110 and an auxiliary structure 6120.

In an example, the air conduit 6000 may be approximately 1 m to 3 m in length, such as 2 m, however it will be understood that any number of lengths may be suitable.

5.6.1 Air Conduit Ends

An air conduit may comprise one or more ends, for example two ends (a patient end and a device end) in a single limb air conduit, and three ends (a device inlet end, a device outlet end and a patient end) in a dual limb air conduit.

An air conduit end may be configured to be connectable to a complementary connector, such to as a circular spigot described in ISO 5356-1 to form a pneumatic connection, or any number of other possible connector designs. Additionally, or alternatively, an air conduit end may be configured to electrically connect to another, complementary apparatus to form a set of electrical connections. Such complementary connectors may be located on an RPT device, a patient interface or an in-line accessory such as a heat-moisture exchanger. Each end may be identical or different to one or more of the other end.

An end may be configured to form one or more pneumatic or electrical connections when connected to a complementary connector. For example, an end may be configured to form a pneumatic connection and electrical connections with an RPT device and/or a humidifier 4000. In another example, an end may be configured to form only a pneumatic connection, such as to connect to a patient interface 3000. It will be obvious that other variations are possible. An electrical connector may be configured to form a plurality of electrical connections, for example as the electrical connector may comprise a plurality of electrical terminals. Each electrical terminal may be electrically connected to an electrical conductor, for example to form an electrical connection to the complementary terminal located on an RPT device.

As an example, an end may comprise a pneumatic connector, such as a fitting comprising a flexible material such as thermoplastic elastomer (TPE). In another example, an end may comprise a fitting comprising a rigid material such as polypropylene. Yet further, an end may comprise a fitting comprising a plurality of materials, for example a rigid material configured to provide structural rigidity and a flexible material configured to provide tactile user touch points.

In the example shown in FIG. 6A, the air conduit 6000 comprises first end 6200 and second end 6300, wherein the second end 6300 comprises an engagement tab 6310, a button 6320 and a keyway 6330 for engaging and disengaging with a complementary component.

5.6.2 Air Conduit Tube Portion

An air conduit may comprise one or more tube portions configured to deliver a flow of air from one end to another end. A single limb air conduit may comprise one tube portion connecting a first end to a second end, allowing air flow between the first end and the second end. A dual limb air conduit may comprise a first tube portion (e.g., an inspiratory limb) connecting a device inlet end to a patient end and a second tube portion (e.g., an expiratory limb) connecting a device outlet end to the patient end.

The tube portion 6100 may comprise a tube wall 6110 (e.g. a polymer film), an electrical conductor (e.g., a copper wire) and an auxiliary structure 6120 (e.g., a helical rib), for example as shown in FIG. 6B.

5.6.2.1 Tube Wall

In the illustrated example, the tube portion 6100 comprises wall 6110 to provide, or define, a path for delivery of the flow of air. For example, the wall 6110 may comprise a thin polymer material suitable to resist expected air pressures (e.g., approximately between 0 to 20 cm $H_2O$ for CPAP therapy) and to adequately prevent damage from usage.

The tube wall 6110 may comprise a polymer, such as polyvinylchloride (PVC) or polyolefin, a textile, or any number of other materials. Another example of a suitable material for tube wall 6110 may be a membrane such as Winstopper® by W. L. Gore & Associates, Inc. The tube wall 6110 may comprise a thickness of between 0.1 mm and 0.3 mm, such as between 0.15 mm and 0.25 mm. The tube wall may comprise a constant thickness or vary its thickness according to its regions.

The tube portion 6100 may comprise a circular cross section as shown in FIG. 6A, although other shapes may also be suitable, such as square, rectangular, oval, hemispheric or others.

It will of course be understood that a number of other materials may also be suitable, in a range of arrangements such as thicknesses, colour and porosity. For example, the tube wall may be thinner where a more flexible property is desired, different coloured tube walls may be used in one air conduit to distinguish between an 'inspiratory' limb and an 'expiratory' limb, and a water vapour permeable membrane may be used for at least a portion of the tube wall.

The tube wall may comprise a cylindrical prism of substantially constant diameter, as shown in FIG. 6B. Additionally, or alternatively, the tube wall may comprise undulations at an angle to an axis of the tube, for example similarly to a bellows or a concertina. The undulations may be configured to increase a local stiffness of the tube wall, such as to resist crushing, and/or to decrease a bending stiffness along a length of the air conduit.

5.6.2.2 Electrical Conductors

The air conduit 6000 may comprise a set of electrical conductors. An electrical conductor may be configured to carry, or transmit, an electrical signal and/or power.

Examples of an electrical conductor include a copper wire and an aluminium wire, as well as a number of other known alternatives. An electrical conductor may extend throughout a length of the air conduit 6000, such as to provide heat to the length of the air conduit 6000. Additionally, or alternatively, an electrical conductor may transmit electrical signal(s) from a first end of the air conduit 6000 to a second end of the air conduit 6000, such as from a sensor located in an end to a humidifier electrically connected to the air conduit 6000.

An air conduit may be configured to provide heat to the flow of air travelling therethrough, for example as described in United States Patent Publication No. 2009/0223514, the entire contents of which are incorporated herewithin by reference. Such heating may function to prevent or reduce occurrence of condensation from the flow of air travelling through the air conduit.

Accordingly, a set of electrical conductors in the air conduit may be configured as a heating element. That is, to provide heat to the flow of air travelling therethrough, one example of which is to configure one or more electrical conductors to function as resistive heaters.

In some forms, an electrical conductor may be configured to carry a multiplexed signal. That is, an electrical conductor may deliver power and signalling, or a plurality of signals superimposed upon each other.

The set of electrical conductors in some forms may comprise a plurality of electrical conductors, such as two, three, or four, extending throughout a length of the air conduit 6000. For example, U.S. Pat. No. 8,733,349 describes an air conduit comprising three electrical conductors extending through a length of the air conduit and forming a part of an electrical circuit.

An electrical conductor may be sized according to one or more requirements, such as material used, intended usage, rate of power to be delivered therethrough, required fidelity of the power and/or data, and any number of other parameters.

In one example, an electrical conductor may be a copper wire of 29 AWG (American Wire Gauge), or 0.289 mm diameter, comprising a wire resistance of 5.1 ohms.

An electrical conductor may require insulation, for fidelity of the electrical signal transmitted thereon, protection of the user from electrical hazards as well as to improve a mechanical reliability of the electrical conductor.

In some forms, an electrical conductor may be enveloped in an insulating sheath. A number of known electrical conductor sheathing material may be suitable, such as a polyvinylchloride (PVC) or polyethylene (LLDPE, MDPE and HDPE).

The insulating sheath may be a tube auxiliary structure, as is described in greater detail elsewhere in the present document.

5.6.2.3 Tube Auxiliary Structure

The tube portion 6100 may comprise one or more auxiliary structures. An auxiliary structure may be configured to increase a rigidity of the tube portion, such as to increase resistance to local deformation (e.g., being crushed, and thus being partly or completely occluded), or provide additional insulation and/or heat, such as to the flow of air travelling therethrough.

The auxiliary structure may be configured to substantially increase local rigidity while limiting an increase in global rigidity, such as measured in a bending stiffness of the air conduit 6000 along its length. As a result, the air conduit 6000 may assume a serpentine configuration along its length in use without inducing excessive forces/moments on the patient and/or the patient interface, which may adversely affect comfort and/or seal.

In the context of the present document, a 'bending stiffness' of the air conduit 6000 along its length, or along its axis, will be taken similarly to a bending stiffness of an engineering structure. A bending stiffness of the air conduit 6000 may be a function of the elastic moduli of the material of the air conduit 6000 and the area moment of inertia. One method by which a bending stiffness of the air conduit 6000 may be determined is by measuring a deflection of the air conduit 6000 (e.g., in the orientation as shown in FIG. 6B, such as fixed at one end) when a force is applied perpendicularly to its axis 6005. Another method of determining a bending stiffness of the air conduit 6000 may be to measure its deformation under gravity, in which case the deformation will be a function of the weight of the air conduit and the bending stiffness.

In some forms, the auxiliary structure may comprise a rib, or a bead, that is helically wound along a length of the air conduit 6000. The rib may be located on a surface (e.g., exterior surface or interior surface) of the tube wall in a helical fashion, such as continuously from one end to another end. The rib may be bonded to the tube wall, such as by an adhesive, mechanically, chemically or may be integrally formed with the wall.

An auxiliary structure may comprise a polymer, such as a low density polyethylene (LDPE), polyvinylchloride (PVC) or polyolefin. Any number of other materials, such as resin-impregnated fabric, may be also suitable. A first auxiliary structure may comprise the same or different materials to a second auxiliary structure. An auxiliary structure and a tube wall may comprise the same or different materials, and may be formed in a single operation.

FIG. 6B shows an example of a portion of the air conduit 6000. In FIG. 6B, the tube portion 6100 comprises tube wall 6110, and an auxiliary structure in the form of a helically wound rib 6120. The tube portion 6100 may be described using language such as a diameter D of the tube portion 6100, a helical pitch P of the rib, a width W of the rib and a height H of the rib (e.g., see FIG. 6B).

In other arrangements, an auxiliary structure may be circumferentially located along the air conduit 6000 (e.g., as a ring) or axially located (e.g., as an axial rib). Of course, a skilled person would appreciate that other auxiliary structures may be also used.

The air conduit 6000 may comprise a plurality of auxiliary structures, such as two, three, or four ribs, none or any number of which may overlap on the air conduit 6000. In one example, the tube portion 6100 may comprise a first rib 6120 and a second rib 6130, each of which may be helically wound along a length of the air conduit 6000, for example as shown in FIGS. 6C-6E.

The first rib 6120 may be axially spaced to the second rib 6130 along the air conduit 6000, by an axial gap G, such as shown in FIG. 6E.

An auxiliary structure may comprise, or encapsulate, an electrical conductor. In some forms, a rib may enclose one, two, three, or any number of wires therein, thus insulating and/or protecting the wires. The rib may helically extend along a length of the air conduit 6000, thereby providing sheathing for the set of electrical conductors throughout the length of the air conduit 6000.

In the context of the present document, an auxiliary structure will be taken to comprise an electrical conductor where the auxiliary structure at least partly surrounds the electrical conductor.

An auxiliary structure may be identically configured to another auxiliary structure in some examples. In other examples, a first auxiliary structure may be differently configured to a second auxiliary structure. A first helical rib may comprise one or more of: a pitch, a material, a height, a cross section shape, a number of electrical conductors, or a coupling method to the tube wall 6110 that differs to a second helical rib.

FIG. 6F shows a portion of the tube portion 6100, taking a cross section along the axis of the tube portion. In the example shown in FIG. 6F, the air conduit 6000 may comprise first auxiliary structure 6120 and second auxiliary structure 6130. In this example, the first auxiliary structure 6120 is a rib, which comprises three electrical conductors, e.g., electrical wires 6151, 6152 and 6153, therein. The second auxiliary structure 6130 is a rib (e.g., a reinforcing rib), not comprising any electrical conductors therein. In an example, the first rib 6120 may comprise a different height to the second reinforcing rib 6130.

In one example, for an air conduit with an internal diameter of approximately 15 mm, the rib 6120 may comprise a height of between 0.5 mm and 2.5 mm, such as between 1 mm and 2 mm, such as between 1.25 mm and 1.75 mm, such as 1.5 mm. A pitch of the rib 6120 may be between 3 mm and 7 mm, such as between 4 mm and 6 mm, 5 mm. A width of the rib may be between 0.5 mm and 3 mm, such as between 1 mm and 2.5 mm, such as between 1.5 mm and 2.5 mm, such as 2 mm.

However, it will be understood that any or all of the above dimensions may be varied according to specific requirements (such as a desired flexibility of the air conduit, required heat output of the air conduit) and/or parameters such as a number of auxiliary structures in the air conduit 6000.

There may be advantages to a tube portion 6100 with a plurality of auxiliary structures, wherein only some of the auxiliary structures comprises at least one electrical conductor.

One advantage may be in reduced costs for the manufacturer and/or subsequently for the consumer. Electrical wires may be costly to produce, particularly for a medical device where high standards of manufacturing may be required. For example, excessive variation in a thickness/diameter of the wire may produce a 'hot spot' on the wire, which may lead to premature failure of the wire, or worse, cause excessive heat which may be hazardous.

Another advantage of the present technology may be to allow separation of functions of the air conduit 6000, such as an electrical function to a mechanical function.

As described above, the air conduit 6000 may be configured to provide one or more functions, including, but not limited to: delivery of a flow of air from one end to another end; delivery of an electrical signal one end to another end; prevention of condensation from the flow of air; delivery of heat to the flow of air; thermal insulation of the flow of air from the ambient; and minimisation of pressure losses in the flow of air.

Each of the one or more air conduit functions is provided by the air conduit 6000 electrically and/or mechanically. By separating a mechanical function (e.g., a local stiffness requirement of the tube portion 6100) from an electrical function (e.g., a heat output requirement of the tube portion 6100), each or both may be better controlled. Such an arrangement may reduce a cost, reduce a weight and/or improve a flexibility of the air conduit.

Accordingly, in some forms of the present technology, the air conduit 6000 may comprise a first auxiliary structure comprising a structural material and an electrical conductor.

An illustrative example will be described below. An exemplary air conduit 6000 (e.g., as shown in FIG. 6A) may comprise only one auxiliary structure 6120, the auxiliary structure 6120 comprising electrical wires for heating. In the exemplary air conduit 6000 shown in FIG. 6A, a change to a pitch of the auxiliary structure 6120 may adjust a mechanical property (e.g., a crush resistance and/or a flexibility), as well as a heat output per length of the air conduit 6000.

In an alternative arrangement such as one shown in FIG. 6D, an air conduit 6000 may comprise a set of auxiliary structures, comprising a first auxiliary structure 6120 and a second auxiliary structure 6130. FIG. 6F shows an exemplary arrangement of the set of auxiliary structures, wherein only the first auxiliary structure 6120 comprises any electrical conductors, the first electrical wire 6151, the second electrical wire 6152, and the third electrical wire 6153.

Thus, the air conduit 6000 may be configured such that only a first subset (the first auxiliary structure) of the set of auxiliary structures may provide a heat output, and a second subset of the set of auxiliary structure may provide a crush resistance (the first and second auxiliary structures).

It will be understood that any number of other configuration of auxiliary structures may be possible. FIGS. 6G-6N show other exemplary arrangements of the present technology.

FIG. 6G shows an arrangement of a tube portion 6100, comprising a tube wall 6110 and two auxiliary structures 6120 and 6130. Both of the two auxiliary structures 6120 and 6130 may be solid ribs, with substantially identical cross section shapes, wherein the first auxiliary structure 6120 comprises electrical wires 6151, 6152 and 6153, and the second auxiliary structure 6130 does not comprise any electrical wires.

Thus, in some arrangements of the present technology, the first auxiliary structure 6120 may comprise a first polymeric material as well as an electrical conductor, and the second auxiliary structure 6130 may consist of a second polymeric material. The auxiliary structures 6120 and 6130 in FIG. 6G are configured such that the first auxiliary structure 6120 is located closer to the second auxiliary structure 6130 in a first direction than in a second direction, i.e., distance 1*d* in first direction is less than distance 2*d* in second direction.

FIG. 6H shows an arrangement of a tube portion 6100, similarly configured to the tube portion 6100 shown in FIG. 6G. In contrast to the tube portion 6100 shown in FIG. 6G, the tube portion 6100 shown in FIG. 6H may be configured that the second auxiliary structure 6130 bisects a pitch of the first auxiliary structure 6120. Thus the first auxiliary structure 6120 is at an identical distance to the second auxiliary structure 6130 in a first direction and in a second direction, i.e., distance 1*d* in first direction is equal to distance 2*d* in second direction.

In the exemplary arrangement of a tube portion 6100 shown in FIG. 6I, the tube portion comprises a tube wall 6110 and two auxiliary structures 6120 and 6130, wherein the two auxiliary structures 6120 and 6130 comprise varying cross section shapes, e.g., the first auxiliary structure 6120 comprises a smaller height and cross-sectional area than the second auxiliary structure 6130. The first auxiliary structure 6120 comprises electrical wires 6151, 6152 and 6153, and the second auxiliary structure 6130 does not comprise any electrical wires.

FIG. 6J shows an arrangement of a tube portion 6100, similarly configured to the tube portion 6100 shown in FIG. 6G. The tube portion 6100 in FIG. 6J comprises a first auxiliary structure 6120 with two electrical wires 6151 and 6152. The first auxiliary structure 6120 comprises a different cross section shape to that of the second auxiliary structure 6130, e.g., the first auxiliary structure 6120 comprises a smaller height and cross-sectional area than the second auxiliary structure 6130. Each electrical wire 6151 and 6152 shown in FIG. 6J is coupled to the first auxiliary structure 6120, being embedded partly in the tube wall 6110 and partly in the first auxiliary structure 6120.

FIG. 6K shows another arrangement of a tube portion 6100, comprising a first auxiliary structure 6120, a second auxiliary structure 6130 and a third auxiliary structure 6140. In this configuration, each of the first auxiliary structure 6120 and the third auxiliary structure 6140 comprise an electrical wire 6151 and 6152 respectively. Each of the first auxiliary structure 6120 and the third auxiliary structure 6140 comprises a first cross section and the second auxiliary structure 6130 comprises a second cross section. In the example shown in FIG. 6K, the first cross section may be significantly smaller than the second cross section, for example comprising an area approximately one fifth, tenth or twentieth the size. Thus, one auxiliary structure (i.e., the second auxiliary structure 6130) may affect a mechanical property of the tube portion 6100 significantly more than another auxiliary structure (i.e., the first auxiliary structure 6120 and/or the third auxiliary structure 6140).

For example, an air conduit 6000 may comprise two auxiliary structures 6120 and 6130, wherein the first auxiliary structure 6120 comprises a height less than 1 mm, such as 0.5 mm, and a width less than 0.8 mm, such as 0.4 mm, and the second auxiliary structure 6130 comprises a height exceeding 1 mm, such as 1.5 mm, and a width exceeding 0.8 mm, such as 1.2 mm.

In another example, an air conduit 6000 may comprise two auxiliary structures 6120 and 6130, wherein the first auxiliary structure 6120 comprises a height and/or a width of less than half of the second auxiliary structure 6130.

FIG. 6L shows an arrangement of a tube portion 6100, similarly configured to the tube portion 6100 shown in FIG. 6K. The tube portion 6100 in FIG. 6J may comprise three auxiliary structures 6120, 6130 and 6140, wherein each auxiliary structure comprises an electrical wire 6151, 6152 and 6153 respectively.

FIG. 6M shows another arrangement of a tube portion 6100, comprising a tube wall 6110 and two auxiliary structures 6120 and 6130. In the example shown in FIG. 6M, the first auxiliary structure 6120 comprises a solid cross section, and the second auxiliary 6130 comprises a hollow cross section, comprising a cavity. The first auxiliary structure 6120 comprises electrical wires 6151, 6152 and 6153, and the second auxiliary structure 6130 does not comprise any electrical wires.

In another example shown in FIG. 6N, both auxiliary structures 6120 and 6130 may comprise hollow cross sections comprising a cavity. The first auxiliary structure 6120 comprises electrical wires 6151, 6152 and 6153, and the second auxiliary structure 6130 does not comprise any electrical wires.

5.6.3 Electrical Components 5.6.3.1 Sensor

In some forms of the present technology, an air conduit may comprise one or more sensors, such as a pressure sensor, a flow rate sensor, a temperature sensor or a humidity sensor. A sensor may produce one or more output signals which may be communicated to a controller such as the central controller 4230 and/or the humidifier controller 5250.

A sensor may be located in, or on, an end of an air conduit in some forms of the present technology. In some forms, a sensor may be located in or on a tube portion of the air conduit. It will be understood that any number of suitable positions may exist for locating a sensor in relation to the air conduit.

It will be clear from the preceding examples that a number of arrangements of an air conduit 6000 may be possible, for example to meet a particular set of design requirements.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Rib: In certain forms of the present technology, a rib may refer to a structure configured to strengthen or support another structure, such as an auxiliary structure configured to strengthen a tube wall. A rib may comprise a solid cross section, or be at least partially hollow in other forms.

Set: In the context of the present document, a set may be taken to mean one or more, such as one, two, three, four, or any other numbers. Thus, a 'set of auxiliary structures' may include one auxiliary structure, or two auxiliary structures.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any sub-range of rational numbers within that range (for example, 2 to 8, 1.5 to 5.5 and 3.1 to 4.7) and, therefore, all sub-ranges of all ranges expressly disclosed herein are hereby also expressly disclosed. These are only examples of what is specifically intended and all possible combinations of numerical values between the lowest value and the highest value enumerated are to be considered to be expressly stated in this application in a similar manner.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 REFERENCE SIGNS LIST

| Feature Item | Number |
| --- | --- |
| patient | 1000 |
| bed partner | 1100 |
| patient interface | 3000 |
| seal-forming structure | 3100 |
| plenum chamber | 3200 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| inlet air filter | 4112 |
| inlet muffler | 4122 |
| outlet muffler | 4124 |
| pressure generator | 4140 |
| blower | 4142 |
| air circuit | 4170 |
| electrical component | 4200 |
| PCBA | 4202 |
| electrical power supply | 4210 |
| input device | 4220 |
| central controller | 4230 |
| therapy device controller | 4240 |
| protection circuit | 4250 |
| memory | 4260 |
| transducer | 4270 |
| pressure sensor | 4272 |
| flow rate sensor | 4274 |
| data communication interface | 4280 |
| output device | 4290 |
| algorithm | 4300 |
| humidifier | 5000 |
| humidifier inlet | 5002 |
| humidifier outlet | 5004 |
| humidifier base | 5006 |

| 5.9 REFERENCE SIGNS LIST | |
| --- | --- |
| Feature Item | Number |
| humidifier reservoir | 5110 |
| humidifier reservoir dock | 5130 |
| heating element | 5240 |
| humidifier controller | 5250 |
| air conduit | 6000 |
| axis | 6005 |
| tube portion | 6100 |
| tube wall | 6110 |
| auxiliary structure | 6120 |
| auxiliary structure | 6130 |
| auxiliary structure | 6140 |
| electrical wire | 6151 |
| electrical wire | 6152 |
| electrical wire | 6153 |
| first end | 6200 |
| second end | 6300 |
| engagement tab | 6310 |
| button | 6320 |
| keyway | 6330 |

The invention claimed is:

1. An air conduit for delivering a flow of air therethrough for respiratory therapy, the air conduit comprising:
a first end configured to form a pneumatic connection with a first respiratory apparatus to receive the flow of air;
a second end configured to form a pneumatic connection with a second respiratory apparatus to deliver the flow of air from the first end; and
a tube portion comprising:
a tube wall defining a path for the flow of air between the first end and the second end;
at least one electrical conductor extending along a length of the tube portion;
a first rib helically wound along the length of the tube portion; and
a second rib helically wound along the length of the tube portion,
wherein the first rib comprises structure that is substantially similar to structure of the second rib,
wherein each of the first rib and the second rib comprises a solid cross-section configured to increase a rigidity of the tube portion,
wherein the first rib is alternately arranged with respect to the second rib along the length of the tube portion,
wherein the first rib is axially spaced from the second rib by an axial gap,
wherein the first rib comprises the at least one electrical conductor, and the second rib forms a reinforcing structure that does not comprise an electrical conductor such that the reinforcing structure is alternately arranged with respect to the at least one electrical conductor along the length of the tube portion,
wherein the second rib forming the reinforcing structure is arranged between a pitch of the first rib including the at least one electrical conductor,
wherein the at least one electrical conductor is encapsulated within the solid cross-section of the first rib so that the first rib provides sheathing for the at least one electrical conductor along the length of the tube portion, and
wherein the first rib is the only structure encapsulating the at least one electrical conductor along the length of the tube portion.

2. The air conduit as claimed in claim 1, wherein the second rib comprises a larger cross-sectional area than the first rib.

3. The air conduit as claimed in claim 1, wherein the second rib comprises a height exceeding 1 mm.

4. The air conduit as claimed in claim 1, wherein the first rib comprises a height less than 1 mm.

5. The air conduit as claimed in claim 1, wherein the first rib and the second rib each comprise a respective first and second pitch, wherein the first pitch is the same as the second pitch.

6. The air conduit as claimed in claim 1, wherein the first rib encapsulates a plurality of the electrical conductor.

7. The air conduit as claimed in claim 1, wherein the at least one electrical conductor comprises a copper wire.

8. The air conduit as claimed in claim 1, wherein the first end is further configured to electrically connect to the first respiratory apparatus.

9. The air conduit as claimed in claim 8, wherein the first end is configured to electrically connect the at least one electrical conductor to the first respiratory apparatus.

10. The air conduit as claimed in claim 1, wherein the first respiratory apparatus is a respiratory pressure therapy device or a humidifier.

11. The air conduit as claimed in claim 1, wherein the second respiratory apparatus is a patient interface.

12. An air conduit for a respiratory apparatus, the air conduit comprising:
a first end comprising a pneumatic connector;
a second end comprising a pneumatic connector; and
a tube portion configured to allow a flow of air between the first end and the second end, the tube portion comprising:
a tube wall defining a path for the flow of air between the first end and the second end;
a first rib extending along a length of the tube portion, the first rib comprising a first polymeric material and at least one electrical wire, wherein the at least one electrical wire extends along the length of the tube portion; and
a second rib extending along the length of the tube portion, the second rib comprising a second polymeric material, wherein the second rib does not comprise an electrical wire,
wherein the first rib comprises structure that is substantially similar to structure of the second rib,
wherein each of the first rib and the second rib comprises a solid cross-section configured to increase a rigidity of the tube portion,
wherein the first rib is alternately arranged with respect to the second rib along the length of the tube portion,
wherein the first rib is axially spaced from the second rib by an axial gap,
wherein the second rib forms a reinforcing structure such that the reinforcing structure is alternately arranged with respect to the at least one electrical wire along the length of the tube portion,
wherein the at least one electrical wire is configured to heat the flow of air,
wherein the second rib is arranged between a pitch of the first rib,
wherein the at least one electrical wire is encapsulated within the solid cross-section of the first rib so that the first rib provides sheathing for the at least one electrical wire along the length of the tube portion, and wherein the first rib is the only structure encapsulating the at least one wire along the length of the tube portion.

13. The air conduit as claimed in claim 12, wherein the first rib comprises a plurality of the electrical wire.

14. The air conduit as claimed in claim 12, wherein the second rib extends helically along the tube portion.

15. The air conduit as claimed in claim 13, wherein at least one of the plurality of the electrical wire is configured to transmit a signal therethrough.

16. The air conduit as claimed in claim 15, wherein the signal is generated by a sensor.

17. The air conduit as claimed in claim 16, wherein the sensor is in the second end.

18. The air conduit as claimed in claim 12, wherein the first polymeric material of the first rib is identical to the second polymeric material of the second rib.

19. The air conduit as claimed in claim 12, wherein the first polymeric material of the first rib is identical to a material of the tube wall of the tube portion.

20. The air conduit as claimed in claim 1, wherein the first rib is axially spaced from the second rib by the axial gap, and the axial gap in a first direction is different than the axial gap in a second direction.

21. The air conduit as claimed in claim 1, wherein the first rib encapsulates three electrical conductors.

22. The air conduit as claimed in claim 1, wherein the second rib is configured and arranged to affect a mechanical property of the tube portion more than the first rib.

23. The air conduit as claimed in claim 1, wherein each of the first rib and the second rib comprises a non-circular cross-section.

24. The air conduit as claimed in claim 1, wherein each of the first rib and the second rib comprises a proximal portion adjacent the tube portion and a distal portion, and wherein a cross-section of each of the first rib and the second rib tapers from a larger width at the distal portion to a smaller width at the proximal portion.

25. The air conduit as claimed in claim 1, wherein each of the first rib and the second rib comprises a flat side wall and a curved top wall.

26. The air conduit as claimed in claim 1, wherein the first rib and the second rib comprise substantially identical cross-sectional shapes.

27. The air conduit as claimed in claim 12, wherein the first rib and the second rib comprise substantially identical cross-sectional shapes.

\* \* \* \* \*